(12) United States Patent
Handique et al.

(10) Patent No.: US 10,975,422 B2
(45) Date of Patent: *Apr. 13, 2021

(54) SYSTEM AND METHOD FOR CAPTURING AND ANALYZING CELLS

(71) Applicant: Bio-Rad Laboratories, Inc., Hercules, CA (US)

(72) Inventors: Kalyan Handique, Ann Arbor, MI (US); Priyadarshini Gogoi, Ann Arbor, MI (US); Saedeh Sepehri Javdani, Ypsilanti, MI (US); Yi Zhou, Ann Arbor, MI (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 290 days.

This patent is subject to a terminal disclaimer.

(21) Appl. No.: 16/049,057

(22) Filed: Jul. 30, 2018

(65) Prior Publication Data

US 2019/0144931 A1 May 16, 2019

Related U.S. Application Data

(63) Continuation of application No. 15/362,565, filed on Nov. 28, 2016, now Pat. No. 10,718,007, which is a continuation of application No. 14/163,185, filed on Jan. 24, 2014, now Pat. No. 9,752,181.

(60) Provisional application No. 61/757,141, filed on Jan. 26, 2013, provisional application No. 61/757,139, filed on Jan. 26, 2013.

(51) Int. Cl.
| | |
|---|---|
| *C12Q 1/68* | (2018.01) |
| *G01N 33/487* | (2006.01) |
| *G01N 33/574* | (2006.01) |
| *C12Q 1/6841* | (2018.01) |
| *C12Q 1/6844* | (2018.01) |
| *C12Q 1/686* | (2018.01) |
| *G01N 27/447* | (2006.01) |

(52) U.S. Cl.
CPC .......... *C12Q 1/6841* (2013.01); *C12Q 1/686* (2013.01); *C12Q 1/6844* (2013.01); *G01N 33/48721* (2013.01); *G01N 33/574* (2013.01); *G01N 33/57492* (2013.01); *G01N 27/44782* (2013.01); *G01N 2333/70585* (2013.01); *G01N 2333/70596* (2013.01)

(58) Field of Classification Search
CPC .... C12Q 1/686; C12Q 1/6841; C12Q 1/6844; G01N 33/48721; G01N 27/44782
See application file for complete search history.

(56) References Cited

U.S. PATENT DOCUMENTS

| | | |
|---|---|---|
| 644,134 A | 2/1900 | Gastineau |
| 4,551,435 A | 11/1985 | Liberti et al. |
| 4,710,635 A | 12/1987 | Chupp |
| 5,266,269 A | 11/1993 | Niiyama et al. |
| 5,491,343 A | 2/1996 | Brooker |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,525,997 B1 | 2/2003 | Narayanaswami et al. |
| 6,563,634 B2 | 5/2003 | Shimada et al. |
| 6,613,525 B2 | 9/2003 | Nelson et al. |
| 6,623,983 B1 | 9/2003 | Terstappen et al. |

(Continued)

FOREIGN PATENT DOCUMENTS

| | | |
|---|---|---|
| CN | 103894248 A | 7/2014 |
| CN | 103998394 A | 8/2014 |

(Continued)

OTHER PUBLICATIONS

European Search Report for application No. 17870743 dated May 26, 2020.

(Continued)

*Primary Examiner* — David C Thomas
(74) *Attorney, Agent, or Firm* — Jeffrey Schox

(57) ABSTRACT

A system and method for capturing and analyzing a set of cells, comprising: an array including a set of parallel pores, each pore including a chamber including a chamber inlet and a chamber outlet, and configured to hold a single cell, and a pore channel fluidly connected to the chamber outlet; an inlet channel fluidly connected to each chamber inlet of the set of parallel pores; an outlet channel fluidly connected to each pore channel of the set of parallel pores; a set of electrophoresis channels fluidly coupled to the outlet channel, configured to receive a sieving matrix for electrophoretic separation; and a set of electrodes including a first electrode and a second electrode, wherein the set of electrodes is configured to provide an electric field that facilitates electrophoretic analysis of the set of cells.

20 Claims, 15 Drawing Sheets

Specification includes a Sequence Listing.

(56) References Cited

U.S. PATENT DOCUMENTS

| | | |
|---|---|---|
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |
| 7,449,558 B2 | 11/2008 | Yao et al. |
| 7,449,778 B2 | 11/2008 | Sander |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,232,112 B2 | 7/2012 | Willson et al. |
| 8,252,517 B2 | 8/2012 | Thomas et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,103,754 B2 | 8/2015 | Handique et al. |
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,513,195 B2 | 12/2016 | Handique et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,746,413 B2 | 8/2017 | Handique et al. |
| 9,752,181 B2 * | 9/2017 | Handique ............ G01N 33/574 |
| 9,757,707 B2 | 9/2017 | Husain et al. |
| 9,802,193 B2 | 10/2017 | Handique et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 10,408,736 B1 | 9/2019 | Handique |
| 10,718,007 B2 * | 7/2020 | Handique ............ C12Q 1/6844 |
| 2002/0119482 A1 | 8/2002 | Nelson et al. |
| 2002/0192808 A1 | 12/2002 | Gambini et al. |
| 2003/0138941 A1 | 7/2003 | Gong et al. |
| 2004/0106130 A1 | 6/2004 | Besemer et al. |
| 2004/0160599 A1 | 8/2004 | Hamamatsu et al. |
| 2004/0229349 A1 | 11/2004 | Daridon |
| 2004/0248318 A1 | 12/2004 | Weinberger et al. |
| 2005/0001176 A1 | 1/2005 | Loney et al. |
| 2005/0014201 A1 | 1/2005 | Deuthsch |
| 2005/0118640 A1 | 6/2005 | Kureshy et al. |
| 2006/0128006 A1 | 6/2006 | Gerhardt et al. |
| 2006/0257992 A1 | 11/2006 | McDevitt et al. |
| 2007/0111302 A1 | 5/2007 | Handique et al. |
| 2007/0238089 A1 | 10/2007 | Rosenthal et al. |
| 2007/0264705 A1 | 11/2007 | Dodgson |
| 2008/0003224 A1 | 1/2008 | Fong et al. |
| 2008/0014589 A1 | 1/2008 | Link et al. |
| 2008/0068588 A1 | 3/2008 | Hess et al. |
| 2008/0090239 A1 | 4/2008 | Shoemaker et al. |
| 2008/0113358 A1 * | 5/2008 | Kapur .................. G01N 33/689 435/6.12 |
| 2008/0124726 A1 | 5/2008 | Monforte |
| 2008/0182273 A1 | 7/2008 | Hansen et al. |
| 2008/0206751 A1 | 8/2008 | Squirrell et al. |
| 2009/0061450 A1 | 3/2009 | Hunter |
| 2009/0081773 A1 | 3/2009 | Kaufman |
| 2009/0141593 A1 | 6/2009 | Taha |
| 2009/0153844 A1 | 6/2009 | Peter et al. |
| 2009/0317836 A1 | 12/2009 | Kuhn et al. |
| 2010/0120077 A1 | 5/2010 | Daridon |
| 2010/0210009 A1 | 8/2010 | Willson et al. |
| 2010/0233693 A1 | 9/2010 | Kopf-Sill et al. |
| 2010/0261179 A1 | 10/2010 | Betley et al. |
| 2010/0291584 A1 | 11/2010 | Tseng et al. |
| 2010/0304485 A1 | 12/2010 | Karnik et al. |
| 2010/0304978 A1 | 12/2010 | Robbins et al. |
| 2011/0003380 A1 | 1/2011 | Miltenyi et al. |
| 2011/0005932 A1 | 1/2011 | Jovanovich et al. |
| 2011/0045994 A1 | 2/2011 | Voldman et al. |
| 2011/0053151 A1 | 3/2011 | Hansen et al. |
| 2011/0117634 A1 | 5/2011 | Halamish et al. |

(56) References Cited

U.S. PATENT DOCUMENTS

| | | |
|---|---|---|
| 2011/0143964 A1 | 6/2011 | Zhou et al. |
| 2011/0227558 A1 | 9/2011 | Mannion et al. |
| 2011/0236904 A1 | 9/2011 | Hauch et al. |
| 2012/0071355 A9 | 3/2012 | Cooney |
| 2012/0129190 A1 | 5/2012 | Chiu et al. |
| 2012/0156675 A1 | 6/2012 | Lueerssen et al. |
| 2012/0164679 A1 | 6/2012 | Vrouwe et al. |
| 2012/0194805 A1 | 8/2012 | Ness et al. |
| 2013/0130376 A1 | 5/2013 | Serobyan et al. |
| 2013/0171628 A1 | 7/2013 | Di et al. |
| 2013/0244906 A1 | 9/2013 | Collins |
| 2014/0173443 A1 | 6/2014 | Hawkins et al. |
| 2014/0213487 A1 | 7/2014 | Freudenthal et al. |
| 2014/0315237 A1 | 10/2014 | Masujima et al. |
| 2014/0357511 A1 | 12/2014 | Handique et al. |
| 2014/0370612 A1 | 12/2014 | Bassler et al. |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0160931 A1 | 6/2015 | Glazer et al. |
| 2015/0376609 A1 | 12/2015 | Hindson et al. |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0130649 A1 | 5/2016 | Xie et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2017/0044525 A1 | 2/2017 | Kaper et al. |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |

FOREIGN PATENT DOCUMENTS

| | | |
|---|---|---|
| CN | 104789468 A | 7/2015 |
| EP | 2414548 A2 | 2/2012 |
| JP | 2008136415 A | 6/2008 |
| WO | 2003035909 A2 | 5/2003 |
| WO | 2006098696 A1 | 9/2006 |
| WO | 2010120818 A2 | 10/2010 |
| WO | 2010142954 A1 | 12/2010 |
| WO | 2015133337 A1 | 9/2015 |
| WO | 2018013723 A1 | 1/2018 |
| WO | 2018058073 A2 | 3/2018 |

OTHER PUBLICATIONS

Seale, K. T. et al. "Mirrored pyramidal wells for simultaneous multiple vantage point microscopy." Journal of Microscopy (2008) 232 1-6. (Year: 2008).

Sugio, Yoshihiro et al. "An agar-based on-chip neural-cell-cultivation system for stepwise control of network pattern generation during cell cultivation." Sensors and Actuators B (2004) 99 156-162. (Year: 2004).

Tan, Wei-Heang et al. "A trap-and-release integrated microfluidic system for dynamic microarray applications." PNAS (2007) 104 1146-1151. (Year 2007).

"Guo, P. et al. Microfluidic capture and release of bacteria in a conical nanopore array. Lab Chip. vol. 12, p. 558-561, 2012, published online Nov. 2011.", Jun. 30, 2017 00:00:00.0.

"Lindstrom, Sara (Royal Institute of Technology, Stockholm, Sweden, 2009, pp. 1-80)".

"Guo, P. et al. Microfluidic capture and release of bacteria in a conical nanopore array. Lab Chip. vol. 12, p. 558-561, 2012, published online Nov. 2011.", Feb. 24, 2016 00:00:00.0.

"Sugio et al. (Sensors and Actuators, B99, 2004, pp. 156-162)".

Tan et al. "A trap-and-release integrated microfluidic system for dynamic microarray applications", PNAS, vol. 104 No. 4, Jan. 23, 2007, pp. 1145-1151.

\* cited by examiner

| Gene | SNP ID | Nucleo-tide change | Wildtype Forward Primer (5'-3') | Mutant Forward Primer (5'-3') | Common Reverse Primer(5'-3') | Amplicon size (bp) |
|---|---|---|---|---|---|---|
| P53 | rs1800371 | C/T | GGCACCAATGGATGATTTGATGCTGTCAC (SEQ ID NO: 4) | TATTAATATTAATTACAATGGATGATTTGATGCTGTCAT (SEQ ID NO: 5) | ATTCTGGGAGCTTCATCTG (SEQ ID NO: 6) | 82 |
| BRCA1 | rs1799967 | A/G | GGCACGGTCAGGCCAGACACCAAT (SEQ ID NO: 7) | TATTAATATTAATTAGGTCAGGCCAGACACCAAC (SEQ ID NO: 8) | CCAATTGAAAGTTGCAGAAT (SEQ ID NO: 9) | 166 |
| BRCA1 | rs4986854 | C/T | GGCACTCTCCCTGCTCACACTTTCTTCAG (SEQ ID NO: 10) | TATTAATATTAATTATCTCCCTGCTCACACTTTCTTCAA (SEQ ID NO: 11) | ACCCTGAATCTGATCCTTCT (SEQ ID NO:12) | 186 |
| BRCA1 | rs1799966 | A/G | GGCACTATGAGCAGCAGCTGGAAT (SEQ ID NO: 13) | TATTAATATTAATTATATGAGCAGCAGCTGGAAC (SEQ ID NO: 14) | TTCAACATTCATCGTTGTGT (SEQ ID NO: 15) | 227 |
| BRCA2 | rs766173 | G/T | GGCACATTGGAAAGTCAATGCCGC (SEQ ID NO: 16) | TATTAATATTAATTAATTGGAAAGTCAATGCCGA (SEQ ID NO: 17) | TGGATCAGTATCATTTGGTTC (SEQ ID NO: 18) | 249 |

FIGURE 13

SEQUENCE LISTING

<160> NUMBER OF SEQ ID NOS: 18

<210> SEQ ID NO 1
<211> LENGTH: 393
<212> TYPE: PRT
<213> ORGANISM: Homo sapiens

<400> SEQUENCE: 1

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Pro Tyr Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
```

-continued

```
                340                 345                 350
Ala Gln Ala Gly Lys Glu Pro Gly Gly Ser Arg Ala His Ser Ser His
            355                 360                 365

Leu Lys Ser Lys Gly Gln Ser Thr Ser Arg His Lys Lys Leu Met
        370                 375                 380

Phe Lys Thr Glu Gly Pro Asp Ser Asp
385                 390

<210> SEQ ID NO 2
<211> LENGTH: 26
<212> TYPE: PRT
<213> ORGANISM: Homo sapiens

<400> SEQUENCE: 2

Met Asp Leu Ser Ala Leu Arg Val Glu Glu Val Gln Asn Val Ile Asn
1               5                   10                  15

Ala Met Gln Lys Ile Leu Glu Cys Pro Ile
            20                  25

<210> SEQ ID NO 3
<211> LENGTH: 3418
<212> TYPE: PRT
<213> ORGANISM: Homo sapiens

<400> SEQUENCE: 3

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
```

|         |         |         |         |         |         | 245     |         |         |         |         | 250     |         |         |         |         | 255     |         |
|---------|---------|---------|---------|---------|---------|---------|---------|---------|---------|---------|---------|---------|---------|---------|---------|---------|---------|

```
Asn Gln Arg Glu Ala Ala Ser His Gly Phe Gly Lys Thr Ser Gly Asn
                260                 265                 270

Ser Phe Lys Val Asn Ser Cys Lys Asp His Ile Gly Lys Ser Met Pro
            275                 280                 285

Asn Val Leu Glu Asp Glu Val Tyr Glu Thr Val Val Asp Thr Ser Glu
            290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
                340                 345                 350

Ser Phe Val Ser Glu Val Glu Pro Asn Asp Thr Asp Pro Leu Asp Ser
                355                 360                 365

Asn Val Ala His Gln Lys Pro Phe Glu Ser Gly Ser Asp Lys Ile Ser
            370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
                420                 425                 430

Asn Lys Arg Lys Lys Asp Phe Leu Thr Ser Glu Asn Ser Leu Pro Arg
                435                 440                 445

Ile Ser Ser Leu Pro Lys Ser Glu Lys Pro Leu Asn Glu Glu Thr Val
            450                 455                 460

Val Asn Lys Arg Asp Glu Glu Gln His Leu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
                500                 505                 510

Lys Glu Thr Phe Asn Ala Ser Phe Ser Gly His Met Thr Asp Pro Asn
            515                 520                 525

Phe Lys Lys Glu Thr Glu Ala Ser Glu Ser Gly Leu Glu Ile His Thr
            530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
                580                 585                 590

Ala Ile His Asp Glu Thr Ser Tyr Lys Gly Lys Lys Ile Pro Lys Asp
                595                 600                 605

Gln Lys Ser Glu Leu Ile Asn Cys Ser Ala Gln Phe Glu Ala Asn Ala
            610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
                660                 665                 670
```

```
Asn Glu Thr Cys Ser Asn Asn Thr Val Ile Ser Gln Asp Leu Asp Tyr
            675                 680                 685

Lys Glu Ala Lys Cys Asn Lys Glu Lys Leu Gln Leu Phe Ile Thr Pro
690                 695                 700

Glu Ala Asp Ser Leu Ser Cys Leu Gln Glu Gly Gln Cys Glu Asn Asp
705                 710                 715                 720

Pro Lys Ser Lys Val Ser Asp Ile Lys Glu Glu Val Leu Ala Ala
                725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
            755                 760                 765

Leu Ile Leu Thr Pro Thr Ser Lys Asp Val Leu Ser Asn Leu Val Met
770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
            835                 840                 845

Val Gln Phe Asn Gln Asn Thr Asn Leu Arg Val Ile Gln Lys Asn Gln
850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
            915                 920                 925

Leu Tyr Gly Asp Thr Gly Asp Lys Gln Ala Thr Gln Val Ser Ile Lys
930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
            995                 1000                1005

Phe Arg Thr Ala Ser Asn Lys Glu Ile Lys Leu Ser Glu His Asn
1010                1015                1020

Ile Lys Lys Ser Lys Met Phe Phe Lys Asp Ile Glu Glu Gln Tyr
    1025                1030                1035

Pro Thr Ser Leu Ala Cys Val Glu Ile Val Asn Thr Leu Ala Leu
    1040                1045                1050

Asp Asn Gln Lys Lys Leu Ser Lys Pro Gln Ser Ile Asn Thr Val
    1055                1060                1065

Ser Ala His Leu Gln Ser Ser Val Val Val Ser Asp Cys Lys Asn
    1070                1075                1080
```

```
Ser His Ile Thr Pro Gln Met Leu Phe Ser Lys Gln Asp Phe Asn
    1085                1090                1095

Ser Asn His Asn Leu Thr Pro Ser Gln Lys Ala Glu Ile Thr Glu
    1100                1105                1110

Leu Ser Thr Ile Leu Glu Glu Ser Gly Ser Gln Phe Glu Phe Thr
    1115                1120                1125

Gln Phe Arg Lys Pro Ser Tyr Ile Leu Gln Lys Ser Thr Phe Glu
    1130                1135                1140

Val Pro Glu Asn Gln Met Thr Ile Leu Lys Thr Thr Ser Glu Glu
    1145                1150                1155

Cys Arg Asp Ala Asp Leu His Val Ile Met Asn Ala Pro Ser Ile
    1160                1165                1170

Gly Gln Val Asp Ser Ser Lys Gln Phe Glu Gly Thr Val Glu Ile
    1175                1180                1185

Lys Arg Lys Phe Ala Gly Leu Leu Lys Asn Asp Cys Asn Lys Ser
    1190                1195                1200

Ala Ser Gly Tyr Leu Thr Asp Glu Asn Glu Val Gly Phe Arg Gly
    1205                1210                1215

Phe Tyr Ser Ala His Gly Thr Lys Leu Asn Val Ser Thr Glu Ala
    1220                1225                1230

Leu Gln Lys Ala Val Lys Leu Phe Ser Asp Ile Glu Asn Ile Ser
    1235                1240                1245

Glu Glu Thr Ser Ala Glu Val His Pro Ile Ser Leu Ser Ser Ser
    1250                1255                1260

Lys Cys His Asp Ser Val Val Ser Met Phe Lys Ile Glu Asn His
    1265                1270                1275

Asn Asp Lys Thr Val Ser Glu Lys Asn Asn Lys Cys Gln Leu Ile
    1280                1285                1290

Leu Gln Asn Asn Ile Glu Met Thr Thr Gly Thr Phe Val Glu Glu
    1295                1300                1305

Ile Thr Glu Asn Tyr Lys Arg Asn Thr Glu Asn Glu Asp Asn Lys
    1310                1315                1320

Tyr Thr Ala Ala Ser Arg Asn Ser His Asn Leu Glu Phe Asp Gly
    1325                1330                1335

Ser Asp Ser Ser Lys Asn Asp Thr Val Cys Ile His Lys Asp Glu
    1340                1345                1350

Thr Asp Leu Leu Phe Thr Asp Gln His Asn Ile Cys Leu Lys Leu
    1355                1360                1365

Ser Gly Gln Phe Met Lys Glu Gly Asn Thr Gln Ile Lys Glu Asp
    1370                1375                1380

Leu Ser Asp Leu Thr Phe Leu Glu Val Ala Lys Ala Gln Glu Ala
    1385                1390                1395

Cys His Gly Asn Thr Ser Asn Lys Glu Gln Leu Thr Ala Thr Lys
    1400                1405                1410

Thr Glu Gln Asn Ile Lys Asp Phe Glu Thr Ser Asp Thr Phe Phe
    1415                1420                1425

Gln Thr Ala Ser Gly Lys Asn Ile Ser Val Ala Lys Glu Ser Phe
    1430                1435                1440

Asn Lys Ile Val Asn Phe Phe Asp Gln Lys Pro Glu Glu Leu His
    1445                1450                1455

Asn Phe Ser Leu Asn Ser Glu Leu His Ser Asp Ile Arg Lys Asn
    1460                1465                1470

Lys Met Asp Ile Leu Ser Tyr Glu Glu Thr Asp Ile Val Lys His
```

-continued

```
            1475                1480                1485
Lys Ile Leu Lys Glu Ser Val Pro Val Gly Thr Gly Asn Gln Leu
            1490                1495                1500
Val Thr Phe Gln Gly Gln Pro Glu Arg Asp Glu Lys Ile Lys Glu
            1505                1510                1515
Pro Thr Leu Leu Gly Phe His Thr Ala Ser Gly Lys Lys Val Lys
            1520                1525                1530
Ile Ala Lys Glu Ser Leu Asp Lys Val Lys Asn Leu Phe Asp Glu
            1535                1540                1545
Lys Glu Gln Gly Thr Ser Glu Ile Thr Ser Phe Ser His Gln Trp
            1550                1555                1560
Ala Lys Thr Leu Lys Tyr Arg Glu Ala Cys Lys Asp Leu Glu Leu
            1565                1570                1575
Ala Cys Glu Thr Ile Glu Ile Thr Ala Ala Pro Lys Cys Lys Glu
            1580                1585                1590
Met Gln Asn Ser Leu Asn Asn Asp Lys Asn Leu Val Ser Ile Glu
            1595                1600                1605
Thr Val Val Pro Pro Lys Leu Leu Ser Asp Asn Leu Cys Arg Gln
            1610                1615                1620
Thr Glu Asn Leu Lys Thr Ser Lys Ser Ile Phe Leu Lys Val Lys
            1625                1630                1635
Val His Glu Asn Val Glu Lys Glu Thr Ala Lys Ser Pro Ala Thr
            1640                1645                1650
Cys Tyr Thr Asn Gln Ser Pro Tyr Ser Val Ile Glu Asn Ser Ala
            1655                1660                1665
Leu Ala Phe Tyr Thr Ser Cys Ser Arg Lys Thr Ser Val Ser Gln
            1670                1675                1680
Thr Ser Leu Leu Glu Ala Lys Lys Trp Leu Arg Glu Gly Ile Phe
            1685                1690                1695
Asp Gly Gln Pro Glu Arg Ile Asn Thr Ala Asp Tyr Val Gly Asn
            1700                1705                1710
Tyr Leu Tyr Glu Asn Asn Ser Asn Ser Thr Ile Ala Glu Asn Asp
            1715                1720                1725
Lys Asn His Leu Ser Glu Lys Gln Asp Thr Tyr Leu Ser Asn Ser
            1730                1735                1740
Ser Met Ser Asn Ser Tyr Ser Tyr His Ser Asp Glu Val Tyr Asn
            1745                1750                1755
Asp Ser Gly Tyr Leu Ser Lys Asn Lys Leu Asp Ser Gly Ile Glu
            1760                1765                1770
Pro Val Leu Lys Asn Val Glu Asp Gln Lys Asn Thr Ser Phe Ser
            1775                1780                1785
Lys Val Ile Ser Asn Val Lys Asp Ala Asn Ala Tyr Pro Gln Thr
            1790                1795                1800
Val Asn Glu Asp Ile Cys Val Glu Glu Leu Val Thr Ser Ser Ser
            1805                1810                1815
Pro Cys Lys Asn Lys Asn Ala Ala Ile Lys Leu Ser Ile Ser Asn
            1820                1825                1830
Ser Asn Asn Phe Glu Val Gly Pro Pro Ala Phe Arg Ile Ala Ser
            1835                1840                1845
Gly Lys Ile Val Cys Val Ser His Glu Thr Ile Lys Lys Val Lys
            1850                1855                1860
Asp Ile Phe Thr Asp Ser Phe Ser Lys Val Ile Lys Glu Asn Asn
            1865                1870                1875
```

```
Glu Asn Lys Ser Lys Ile Cys Gln Thr Lys Ile Met Ala Gly Cys
    1880                1885                1890

Tyr Glu Ala Leu Asp Asp Ser Glu Asp Ile Leu His Asn Ser Leu
    1895                1900                1905

Asp Asn Asp Glu Cys Ser Thr His Ser His Lys Val Phe Ala Asp
    1910                1915                1920

Ile Gln Ser Glu Glu Ile Leu Gln His Asn Gln Asn Met Ser Gly
    1925                1930                1935

Leu Glu Lys Val Ser Lys Ile Ser Pro Cys Asp Val Ser Leu Glu
    1940                1945                1950

Thr Ser Asp Ile Cys Lys Cys Ser Ile Gly Lys Leu His Lys Ser
    1955                1960                1965

Val Ser Ser Ala Asn Thr Cys Gly Ile Phe Ser Thr Ala Ser Gly
    1970                1975                1980

Lys Ser Val Gln Val Ser Asp Ala Ser Leu Gln Asn Ala Arg Gln
    1985                1990                1995

Val Phe Ser Glu Ile Glu Asp Ser Thr Lys Gln Val Phe Ser Lys
    2000                2005                2010

Val Leu Phe Lys Ser Asn Glu His Ser Asp Gln Leu Thr Arg Glu
    2015                2020                2025

Glu Asn Thr Ala Ile Arg Thr Pro Glu His Leu Ile Ser Gln Lys
    2030                2035                2040

Gly Phe Ser Tyr Asn Val Val Asn Ser Ser Ala Phe Ser Gly Phe
    2045                2050                2055

Ser Thr Ala Ser Gly Lys Gln Val Ser Ile Leu Glu Ser Ser Leu
    2060                2065                2070

His Lys Val Lys Gly Val Leu Glu Glu Phe Asp Leu Ile Arg Thr
    2075                2080                2085

Glu His Ser Leu His Tyr Ser Pro Thr Ser Arg Gln Asn Val Ser
    2090                2095                2100

Lys Ile Leu Pro Arg Val Asp Lys Arg Asn Pro Glu His Cys Val
    2105                2110                2115

Asn Ser Glu Met Glu Lys Thr Cys Ser Lys Glu Phe Lys Leu Ser
    2120                2125                2130

Asn Asn Leu Asn Val Glu Gly Gly Ser Ser Glu Asn Asn His Ser
    2135                2140                2145

Ile Lys Val Ser Pro Tyr Leu Ser Gln Phe Gln Gln Asp Lys Gln
    2150                2155                2160

Gln Leu Val Leu Gly Thr Lys Val Ser Leu Val Glu Asn Ile His
    2165                2170                2175

Val Leu Gly Lys Glu Gln Ala Ser Pro Lys Asn Val Lys Met Glu
    2180                2185                2190

Ile Gly Lys Thr Glu Thr Phe Ser Asp Val Pro Val Lys Thr Asn
    2195                2200                2205

Ile Glu Val Cys Ser Thr Tyr Ser Lys Asp Ser Glu Asn Tyr Phe
    2210                2215                2220

Glu Thr Glu Ala Val Glu Ile Ala Lys Ala Phe Met Glu Asp Asp
    2225                2230                2235

Glu Leu Thr Asp Ser Lys Leu Pro Ser His Ala Thr His Ser Leu
    2240                2245                2250

Phe Thr Cys Pro Glu Asn Glu Glu Met Val Leu Ser Asn Ser Arg
    2255                2260                2265
```

```
Ile Gly Lys Arg Arg Gly Glu Pro Leu Ile Leu Val Gly Glu Pro
2270                2275                2280

Ser Ile Lys Arg Asn Leu Leu Asn Glu Phe Asp Arg Ile Ile Glu
2285                2290                2295

Asn Gln Glu Lys Ser Leu Lys Ala Ser Lys Ser Thr Pro Asp Gly
2300                2305                2310

Thr Ile Lys Asp Arg Arg Leu Phe Met His His Val Ser Leu Glu
2315                2320                2325

Pro Ile Thr Cys Val Pro Phe Arg Thr Thr Lys Glu Arg Gln Glu
2330                2335                2340

Ile Gln Asn Pro Asn Phe Thr Ala Pro Gly Gln Glu Phe Leu Ser
2345                2350                2355

Lys Ser His Leu Tyr Glu His Leu Thr Leu Glu Lys Ser Ser Ser
2360                2365                2370

Asn Leu Ala Val Ser Gly His Pro Phe Tyr Gln Val Ser Ala Thr
2375                2380                2385

Arg Asn Glu Lys Met Arg His Leu Ile Thr Thr Gly Arg Pro Thr
2390                2395                2400

Lys Val Phe Val Pro Pro Phe Lys Thr Lys Ser His Phe His Arg
2405                2410                2415

Val Glu Gln Cys Val Arg Asn Ile Asn Leu Glu Glu Asn Arg Gln
2420                2425                2430

Lys Gln Asn Ile Asp Gly His Gly Ser Asp Asp Ser Lys Asn Lys
2435                2440                2445

Ile Asn Asp Asn Glu Ile His Gln Phe Asn Lys Asn Asn Ser Asn
2450                2455                2460

Gln Ala Ala Ala Val Thr Phe Thr Lys Cys Glu Glu Glu Pro Leu
2465                2470                2475

Asp Leu Ile Thr Ser Leu Gln Asn Ala Arg Asp Ile Gln Asp Met
2480                2485                2490

Arg Ile Lys Lys Lys Gln Arg Gln Arg Val Phe Pro Gln Pro Gly
2495                2500                2505

Ser Leu Tyr Leu Ala Lys Thr Ser Thr Leu Pro Arg Ile Ser Leu
2510                2515                2520

Lys Ala Ala Val Gly Gly Gln Val Pro Ser Ala Cys Ser His Lys
2525                2530                2535

Gln Leu Tyr Thr Tyr Gly Val Ser Lys His Cys Ile Lys Ile Asn
2540                2545                2550

Ser Lys Asn Ala Glu Ser Phe Gln Phe His Thr Glu Asp Tyr Phe
2555                2560                2565

Gly Lys Glu Ser Leu Trp Thr Gly Lys Gly Ile Gln Leu Ala Asp
2570                2575                2580

Gly Gly Trp Leu Ile Pro Ser Asn Asp Gly Lys Ala Gly Lys Glu
2585                2590                2595

Glu Phe Tyr Arg Ala Leu Cys Asp Thr Pro Gly Val Asp Pro Lys
2600                2605                2610

Leu Ile Ser Arg Ile Trp Val Tyr Asn His Tyr Arg Trp Ile Ile
2615                2620                2625

Trp Lys Leu Ala Ala Met Glu Cys Ala Phe Pro Lys Glu Phe Ala
2630                2635                2640

Asn Arg Cys Leu Ser Pro Glu Arg Val Leu Leu Gln Leu Lys Tyr
2645                2650                2655

Arg Tyr Asp Thr Glu Ile Asp Arg Ser Arg Arg Ser Ala Ile Lys
```

-continued

|  |  |  | 2660 |  |  |  | 2665 |  |  |  | 2670 |
| --- | --- | --- | --- | --- | --- | --- | --- | --- | --- | --- | --- |

Lys Ile Met Glu Arg Asp Asp Thr Ala Ala Lys Thr Leu Val Leu
        2675                    2680                    2685

Cys Val Ser Asp Ile Ile Ser Leu Ser Ala Asn Ile Ser Glu Thr
        2690                    2695                    2700

Ser Ser Asn Lys Thr Ser Ser Ala Asp Thr Gln Lys Val Ala Ile
        2705                    2710                    2715

Ile Glu Leu Thr Asp Gly Trp Tyr Ala Val Lys Ala Gln Leu Asp
        2720                    2725                    2730

Pro Pro Leu Leu Ala Val Leu Lys Asn Gly Arg Leu Thr Val Gly
        2735                    2740                    2745

Gln Lys Ile Ile Leu His Gly Ala Glu Leu Val Gly Ser Pro Asp
        2750                    2755                    2760

Ala Cys Thr Pro Leu Glu Ala Pro Glu Ser Leu Met Leu Lys Ile
        2765                    2770                    2775

Ser Ala Asn Ser Thr Arg Pro Ala Arg Trp Tyr Thr Lys Leu Gly
        2780                    2785                    2790

Phe Phe Pro Asp Pro Arg Pro Phe Pro Leu Pro Leu Ser Ser Leu
        2795                    2800                    2805

Phe Ser Asp Gly Gly Asn Val Gly Cys Val Asp Val Ile Ile Gln
        2810                    2815                    2820

Arg Ala Tyr Pro Ile Gln Trp Met Glu Lys Thr Ser Ser Gly Leu
        2825                    2830                    2835

Tyr Ile Phe Arg Asn Glu Arg Glu Glu Glu Lys Glu Ala Ala Lys
        2840                    2845                    2850

Tyr Val Glu Ala Gln Gln Lys Arg Leu Glu Ala Leu Phe Thr Lys
        2855                    2860                    2865

Ile Gln Glu Glu Phe Glu Glu His Glu Glu Asn Thr Thr Lys Pro
        2870                    2875                    2880

Tyr Leu Pro Ser Arg Ala Leu Thr Arg Gln Gln Val Arg Ala Leu
        2885                    2890                    2895

Gln Asp Gly Ala Glu Leu Tyr Glu Ala Val Lys Asn Ala Ala Asp
        2900                    2905                    2910

Pro Ala Tyr Leu Glu Gly Tyr Phe Ser Glu Glu Gln Leu Arg Ala
        2915                    2920                    2925

Leu Asn Asn His Arg Gln Met Leu Asn Asp Lys Lys Gln Ala Gln
        2930                    2935                    2940

Ile Gln Leu Glu Ile Arg Lys Ala Met Glu Ser Ala Glu Gln Lys
        2945                    2950                    2955

Glu Gln Gly Leu Ser Arg Asp Val Thr Thr Val Trp Lys Leu Arg
        2960                    2965                    2970

Ile Val Ser Tyr Ser Lys Lys Glu Lys Asp Ser Val Ile Leu Ser
        2975                    2980                    2985

Ile Trp Arg Pro Ser Ser Asp Leu Tyr Ser Leu Leu Thr Glu Gly
        2990                    2995                    3000

Lys Arg Tyr Arg Ile Tyr His Leu Ala Thr Ser Lys Ser Lys Ser
        3005                    3010                    3015

Lys Ser Glu Arg Ala Asn Ile Gln Leu Ala Ala Thr Lys Lys Thr
        3020                    3025                    3030

Gln Tyr Gln Gln Leu Pro Val Ser Asp Glu Ile Leu Phe Gln Ile
        3035                    3040                    3045

Tyr Gln Pro Arg Glu Pro Leu His Phe Ser Lys Phe Leu Asp Pro
        3050                    3055                    3060

```
Asp Phe Gln Pro Ser Cys Ser Glu Val Asp Leu Ile Gly Phe Val
3065                3070                3075

Val Ser Val Val Lys Lys Thr Gly Leu Ala Pro Phe Val Tyr Leu
3080                3085                3090

Ser Asp Glu Cys Tyr Asn Leu Leu Ala Ile Lys Phe Trp Ile Asp
3095                3100                3105

Leu Asn Glu Asp Ile Ile Lys Pro His Met Leu Ile Ala Ala Ser
3110                3115                3120

Asn Leu Gln Trp Arg Pro Glu Ser Lys Ser Gly Leu Leu Thr Leu
3125                3130                3135

Phe Ala Gly Asp Phe Ser Val Phe Ser Ala Ser Pro Lys Glu Gly
3140                3145                3150

His Phe Gln Glu Thr Phe Asn Lys Met Lys Asn Thr Val Glu Asn
3155                3160                3165

Ile Asp Ile Leu Cys Asn Glu Ala Glu Asn Lys Leu Met His Ile
3170                3175                3180

Leu His Ala Asn Asp Pro Lys Trp Ser Thr Pro Thr Lys Asp Cys
3185                3190                3195

Thr Ser Gly Pro Tyr Thr Ala Gln Ile Ile Pro Gly Thr Gly Asn
3200                3205                3210

Lys Leu Leu Met Ser Ser Pro Asn Cys Glu Ile Tyr Tyr Gln Ser
3215                3220                3225

Pro Leu Ser Leu Cys Met Ala Lys Arg Lys Ser Val Ser Thr Pro
3230                3235                3240

Val Ser Ala Gln Met Thr Ser Lys Ser Cys Lys Gly Glu Lys Glu
3245                3250                3255

Ile Asp Asp Gln Lys Asn Cys Lys Lys Arg Arg Ala Leu Asp Phe
3260                3265                3270

Leu Ser Arg Leu Pro Leu Pro Pro Pro Val Ser Pro Ile Cys Thr
3275                3280                3285

Phe Val Ser Pro Ala Ala Gln Lys Ala Phe Gln Pro Pro Arg Ser
3290                3295                3300

Cys Gly Thr Lys Tyr Glu Thr Pro Ile Lys Lys Lys Glu Leu Asn
3305                3310                3315

Ser Pro Gln Met Thr Pro Phe Lys Lys Phe Asn Glu Ile Ser Leu
3320                3325                3330

Leu Glu Ser Asn Ser Ile Ala Asp Glu Glu Leu Ala Leu Ile Asn
3335                3340                3345

Thr Gln Ala Leu Leu Ser Gly Ser Thr Gly Glu Lys Gln Phe Ile
3350                3355                3360

Ser Val Ser Glu Ser Thr Arg Thr Ala Pro Thr Ser Ser Glu Asp
3365                3370                3375

Tyr Leu Arg Leu Lys Arg Arg Cys Thr Thr Ser Leu Ile Lys Glu
3380                3385                3390

Gln Glu Ser Ser Gln Ala Ser Thr Glu Glu Cys Glu Lys Asn Lys
3395                3400                3405

Gln Asp Thr Ile Thr Thr Lys Lys Tyr Ile
3410                3415

<210> SEQ ID NO 4
<211> LENGTH: 29
<212> TYPE: DNA
<213> ORGANISM: Homo sapiens
```

```
<400> SEQUENCE: 4
ggcaccaatg gatgatttga tgctgtcac                                    29

<210> SEQ ID NO 5
<211> LENGTH: 38
<212> TYPE: DNA
<213> ORGANISM: Homo sapiens

<400> SEQUENCE: 5
tattaatatt aattacaatg gatgattgat gctgtcat                          38

<210> SEQ ID NO 6
<211> LENGTH: 19
<212> TYPE: DNA
<213> ORGANISM: Homo sapiens

<400> SEQUENCE: 6
attctgggag cttcatctg                                               19

<210> SEQ ID NO 7
<211> LENGTH: 24
<212> TYPE: DNA
<213> ORGANISM: Homo sapiens

<400> SEQUENCE: 7
ggcacggtca ggccagacac caat                                         24

<210> SEQ ID NO 8
<211> LENGTH: 34
<212> TYPE: DNA
<213> ORGANISM: Homo sapiens

<400> SEQUENCE: 8
tattaatatt aattaggtca ggccagacac caac                              34

<210> SEQ ID NO 9
<211> LENGTH: 20
<212> TYPE: DNA
<213> ORGANISM: Homo sapiens

<400> SEQUENCE: 9
ccaattgaaa gttgcagaat                                              20

<210> SEQ ID NO 10
<211> LENGTH: 29
<212> TYPE: DNA
<213> ORGANISM: Homo sapiens

<400> SEQUENCE: 10
ggcactctcc ctgctcacac tttcttcag                                    29

<210> SEQ ID NO 11
<211> LENGTH: 39
<212> TYPE: DNA
<213> ORGANISM: Homo sapiens

<400> SEQUENCE: 11
tattaatatt aattatctcc ctgctcacac tttcttcaa                         39

<210> SEQ ID NO 12
<211> LENGTH: 20
<212> TYPE: DNA
<213> ORGANISM: Homo sapiens
```

```
<400> SEQUENCE: 12
accctgaatc tgatccttct                                                    20

<210> SEQ ID NO 13
<211> LENGTH: 24
<212> TYPE: DNA
<213> ORGANISM: Homo sapiens

<400> SEQUENCE: 13
ggcactatga gcagcagctg gaat                                               24

<210> SEQ ID NO 14
<211> LENGTH: 34
<212> TYPE: DNA
<213> ORGANISM: Homo sapiens

<400> SEQUENCE: 14
tattaatatt aattatatga gcagcagctg gaac                                    34

<210> SEQ ID NO 15
<211> LENGTH: 20
<212> TYPE: DNA
<213> ORGANISM: Homo sapiens

<400> SEQUENCE: 15
ttcaacattc atcgttgtgt                                                    20

<210> SEQ ID NO 16
<211> LENGTH: 24
<212> TYPE: DNA
<213> ORGANISM: Homo sapiens

<400> SEQUENCE: 16
ggcacattgg aaagtcaatg ccgc                                               24

<210> SEQ ID NO 17
<211> LENGTH: 34
<212> TYPE: DNA
<213> ORGANISM: Homo sapiens

<400> SEQUENCE: 17
tattaatatt aattaattgg aaagtcaatg ccga                                    34

<210> SEQ ID NO 18
<211> LENGTH: 21
<212> TYPE: DNA
<213> ORGANISM: Homo sapiens

<400> SEQUENCE: 18
tggatcagta tcatttggtt c                                                  21
```

SYSTEM AND METHOD FOR CAPTURING AND ANALYZING CELLS

CROSS-REFERENCE TO RELATED APPLICATIONS

This application is a continuation of U.S. patent application Ser. No. 15/362,565, filed 28 Nov. 2016, which is a continuation of U.S. patent application Ser. No. 14/163,185, filed 24 Jan. 2014, which claims the benefit of U.S. Provisional Application No. 61/757,141 filed on 26 Jan. 2013 and U.S. Provisional Application No. 61/757,139 filed on 26 Jan. 2013, all of which are incorporated in their entirety herein by this reference.

TECHNICAL FIELD

This invention relates generally to the cell sorting field, and more specifically to a new and useful system and method for capturing and analyzing cells within the cell sorting field.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting systems are becoming highly desirable. However, preexisting cell capture systems suffer from various shortcomings that prevent widespread adoption for cell-specific testing. For example, flow cytometry requires that the cell be simultaneously identified and sorted, and limits cell observation to a single instance. Flow cytometry fails to allow for multiple analyses of the same cell, and does not permit arbitrary cell subpopulation sorting. Conventional microfluidic devices rely on cell-specific antibodies for cell selection, wherein the antibodies that are bound to the microfluidic device substrate selectively bind to cells expressing the desired antigen. Conventional microfluidic devices can also fail to allow for subsequent cell removal without cell damage, and only capture the cells expressing the specific antigen; non-expressing cells, which could also be desired, are not captured by these systems. Cellular filters can separate sample components based on size without significant cell damage, but suffer from clogging and do not allow for specific cell identification, isolation of individual cells, and retrieval of identified individual cells. Other technologies in this field are further limited in their ability to allow multiplex assays to be performed on individual cells, while minimizing sample preparation steps.

Thus, there is a need in the cell sorting field to create a new and useful cell system and method for capturing and analyzing cells.

BRIEF DESCRIPTION OF THE FIGURES

FIGS. 7A-7D are side views of a first, second, third and fourth optical element, respectively;

FIG. 13 depicts a portion of an embodiment of a method for capturing and analyzing cells, including specific forward and reverse primers for AS-PCR;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1A:
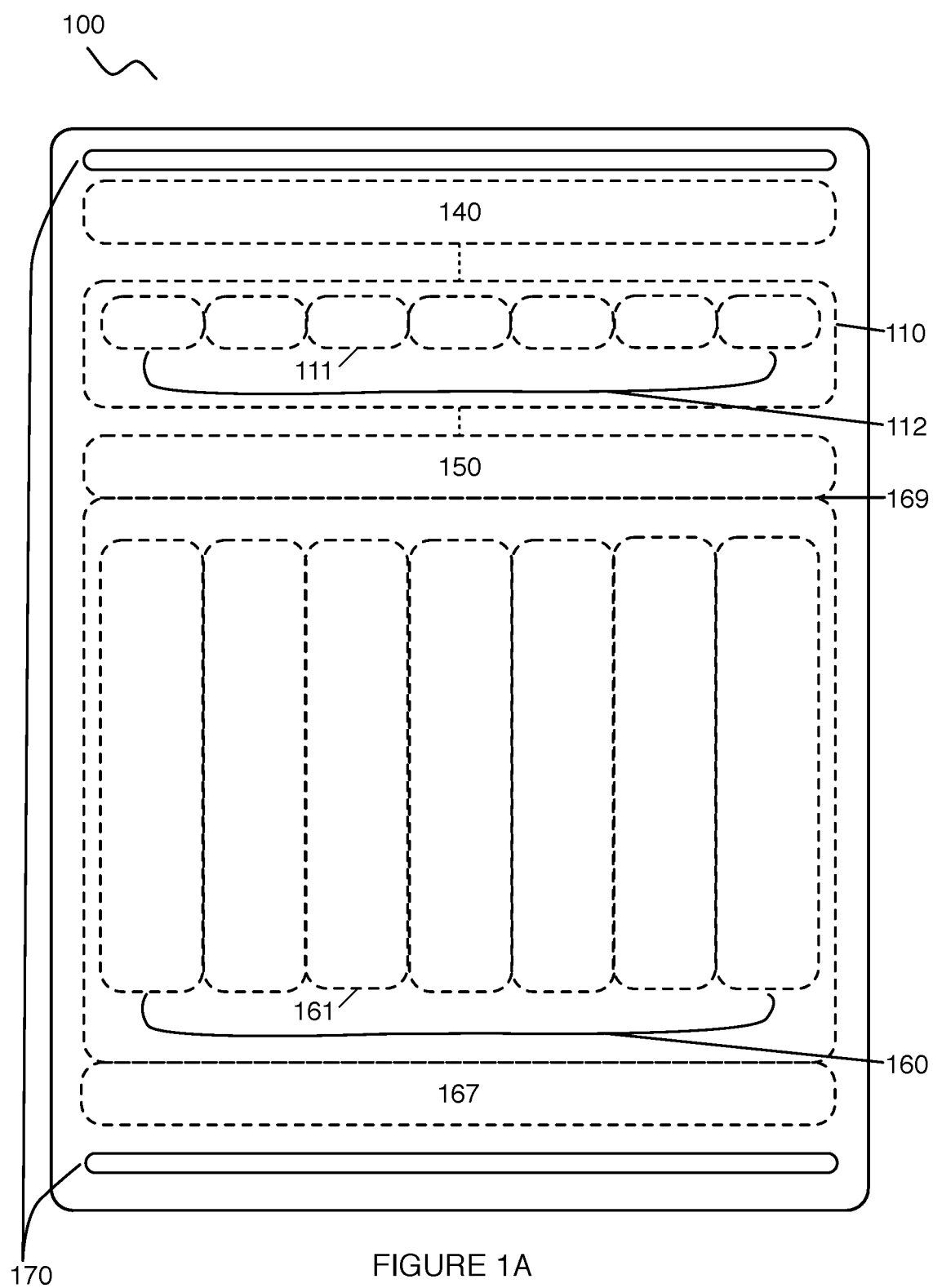
FIG. 1A is a schematic representation of an embodiment of a system for capturing and analyzing cells.
Figure 1B:
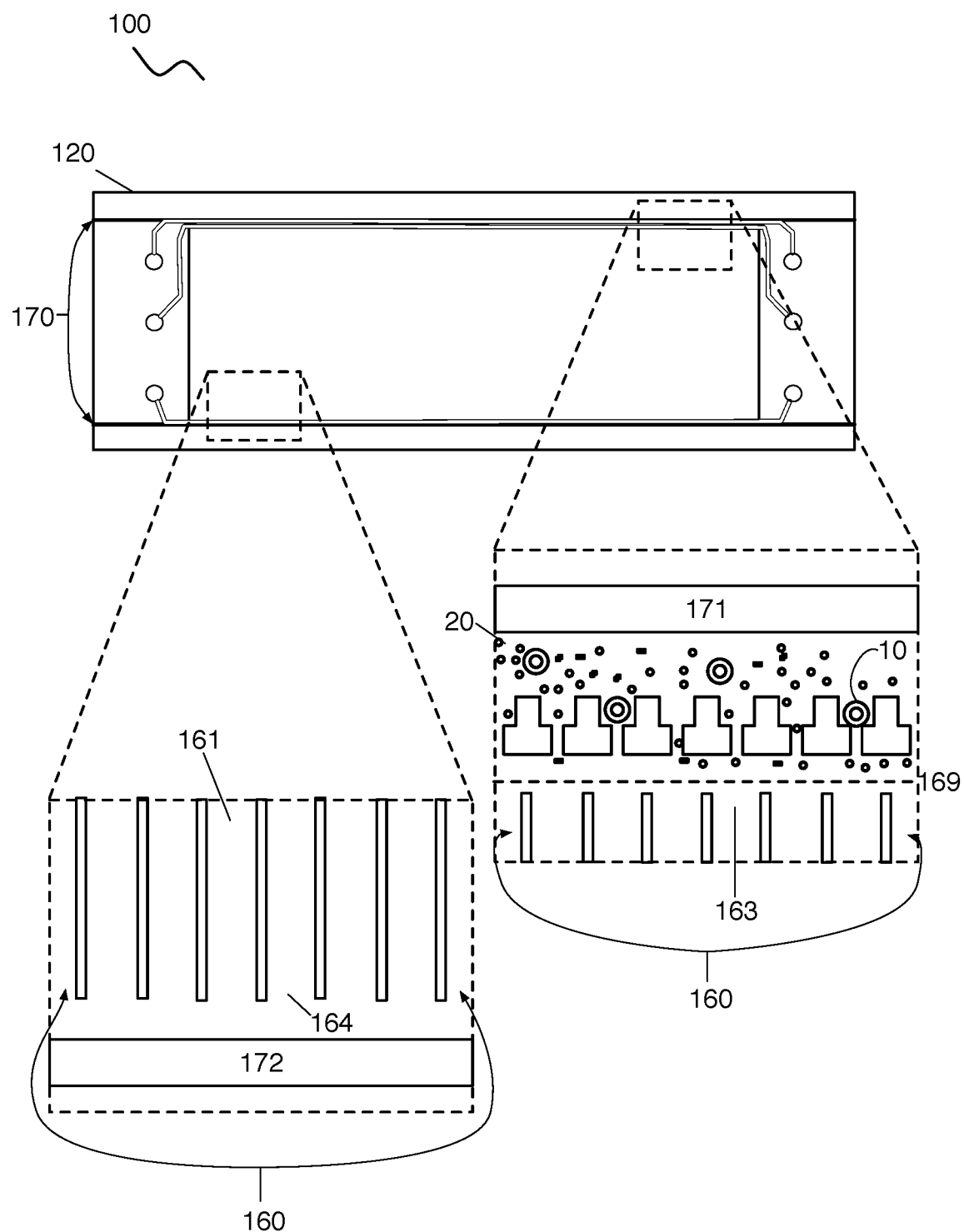
FIG. 1B depicts a variation of an embodiment of a system for capturing and analyzing cells.
Figure 1C:
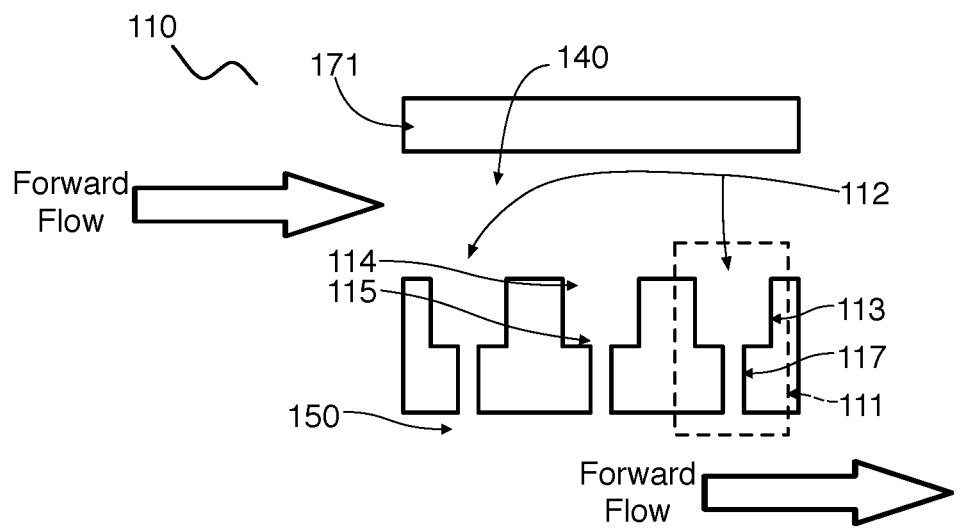
FIG. 1C is a perspective view of a variation of the system.

As shown in FIGS. 1A, 1B, and 1C, a system 100 for capturing and analyzing a set of cells comprises: an array 110 including a set of pores 112, each pore 111 configured to hold a single cell of the set of cells; an inlet channel 140 coupled to an inlet of each pore; an outlet channel 150 coupled to an outlet of each pore; a set of electrophoresis channels 160 fluidly coupled to the outlet channel, each electrophoresis channel 161 aligned with a pore of the set of pores; and a set of electrodes 170 configured to provide an electric field that facilitates electrophoretic analysis of the set of cells. In one embodiment, the array 110 includes a set of pores 112, each pore 111 including a chamber 113 including a chamber inlet 114 and a chamber outlet 115 fluidly connected to a pore channel 117; the inlet channel 140 is fluidly connected to each chamber inlet of the set of pores 112; and the outlet channel 150 is fluidly connected to each the pore channel 117 of the set of pores 112.

The system 100 functions to isolate, capture, and hold cells, more preferably single cells, at known, addressable locations, and further to facilitate performance of multiple single-cell assays that can be performed on individual cells (e.g., rare cells in a biological sample). Once cells are captured in defined locations determined by single cell capture chambers, a fluidic network of the system 100 can be used to provide and deliver multiple reagents simultaneously or sequentially to enable a variety of cellular, sub-cellular or molecular reactions to be performed in each of the single cells. The system 100 can also allow optical interrogation and detection of events on each of the captured cells at a single cell level. The system 100 can additionally enable selective release and/or selective removal of one or more of the captured cells for further processing and analysis. In some embodiments, the system 100 can confer the benefits of real-time cell tracking, viable cell retrieval, and selective downstream molecular analysis (e.g., electrophoresis), either in the same microfluidic chip or off-chip. In some embodiments, the system 100 can be used to capture circulating tumor cells (CTCs) and subpopulations of CTCs, such as circulating stem cells (CSCs), but can additionally or alternatively be used to capture any other suitable cell of possible interest. The system 100 is preferably defined on a chip, more preferably a microfluidic chip, but can alternatively be located on or defined by any suitable substrate 120.

The system 100 preferably achieves individual cell capture and retention without antibody coated chambers 113, and preferably maintains the viability of the cells throughout isolation, capture, retention, and removal. The system 100 preferably additionally minimizes clogging, and can accomplish this by utilizing suitably sized pores in and by leveraging massively parallel flow, such that the cells near a sample inlet 122 configured to transmit the set of cells toward the array preferably experience substantially the same pressure as the cells distal the sample inlet 122 while minimizing the total pressure differential required to flow liquid at high rates through the system 100. The variation in pressure felt by cells at the respective ends of the array is preferably less than 50% or 75% of the inlet pressure, but can alternatively be more or less. The sample flow is preferably substantially laminar, but can alternatively have any other suitable flow characteristics. The sample flow path is preferably substantially unidirectional, but can alternatively be bi-directional. Cell sorting and viability maintenance can additionally be accomplished by controlling the sample flow rate through the system, or through any other suitable means.

In operation, the system 100 preferably receives a biological sample including the set of cells under positive pressure through the sample inlet 122, which can be coupled to a fluid channel (e.g., an inlet manifold) coupled to a pump configured to provide the positive pressure. Sample flow through the system 100 can be additionally or alternatively encouraged by providing negative pressure at an outlet (e.g., at an outlet manifold coupled to an outlet of the array). Alternatively, actuation pressure can be cycled in a pulse-width modulation fashion or sinusoidal fashion to provide net actuation pressure, either net positive at the inlet or net negative at the outlet. The sample preferably flows into the inlet channel 140, through the chambers 113 and pore channels 117 to the outlet channel 150, with the set of cells being captured in the chambers 113 for further processing and analysis, and other sample components passing out of the system 100. As such, desired cells of a predetermined size are preferably trapped within the chamber 113 as the sample flows through the pores 111, wherein the pore channel 117 dimensions preferably prevent flow of certain cell sizes therethrough. For example, in the variation of the system 100 configured to capture CTCs, the chambers 113 are preferably dimensioned larger than a CTC, and the pore channels 117 are preferably dimensioned smaller than the CTC (but larger than other undesired components in the biological sample, to allow passage of the undesired components. However, the system 100 can additionally or alternatively be configured to retain and facilitate processing or any other suitable particle of interest.

1.1 System—Array

The array 110 functions to capture a set of cells of interest in addressable, known locations, as shown in FIGS. 1B and 1C, such that the set of cells can be individually identified, processed, and analyzed. As shown in FIG. 1C, the array 110 includes a set of pores 112, each pore 111 including a chamber 113 defining a chamber inlet 114 and a chamber outlet 115 fluidly connected to a pore channel 117. In embodiments, the inlet channel 140 of the system 100 is preferably fluidly coupled to each chamber inlet 114 of the set of pores 112; and the outlet channel 150 of the system 100 is preferably fluidly coupled to each pore channel 117 of the set of pores 112. However, the inlet channel 140 can alternatively be configured to fluidly couple to only a portion of chamber inlets 114 of the set of pores 112, and/or the outlet channel 150 can be configured to fluidly couple to only a portion of the pore channels 117 of the set of pores 112 (e.g., in configurations wherein some of the pores are coupled in series). Preferably, the array 110 is defined within a substrate 120, by forming microfluidic elements within the substrate 120 (e.g., by etching); however, the array 110 can be formed in any other suitable manner (e.g., by lithography, by molding, by 3D printing, by micromachining, by casting, etc.). The substrate 120 can be the substrate described in U.S. Pub. No. 2013/0190212, entitled "Cell Capture System and Method of Use" filed 25 Jul. 2012, which is incorporated herein in its entirety by this reference. In a specific example, the array 110 is defined within a 4-inch silicon substrate using a three mask photolithographic process and deep reactive ion etching (DRIE) process to etch microfluidic elements into the silicon substrate as a mold. In the specific example, the etched elements are then transferred to 1 millimeter thick polymethylmethacrylate (PMMA) sheets as a substrate 120 using a hot embossing process, which is then laminated with a polymethylmethacrylate (PMMA) laminate to define microfluidic pathways. In the specific example, lamination includes utilizing an appropriate roller speed, temperature, pressure, and tension of the laminate to ensure a low level of ingress of laminate material into microfluidic structures. The substrate 120 in the specific example has dimensions of 75 millimeters by 25 millimeters, in order to substantially match dimensions of a glass microscope slide. However, the substrate 120 can alternatively be any other suitable substrate 120. In variations of the specific example, and/or for other variations of the array 110, hot embossing of cyclic olefin polymer (COP) can be substituted for PMMA to form the microfluidic structures of the array. Alternatively, the microfluidic device can be assembled (e.g., prior to running experiments) by coupling (e.g., uniformly pressing) a substrate 120 containing the microstructures against an elastomeric substrate without permanently adhering to a laminate.

The array 110 is preferably substantially linear with a substantially constant width, but can alternatively be non-linear and/or have a variable width. The array 110 preferably includes a linear inlet channel 140, a linear outlet channel 150 arranged parallel to the inlet channel 140, and a set of parallel pores 112 arranged therebetween, as shown in FIG. 1C, normal to the inlet channel 140 and the outlet channel 150, in a manner that fluidly couples the inlet channel 140 and the outlet channel 150 to the set of parallel pores 112. However, the array 110 can alternatively be substantially linear with a diverging or converging width, wherein the inlet channel 140 and the outlet channel 150 are arranged at an angle, and consecutive pores 111 have increasing or decreasing lengths. The array 110 can alternatively be serpentine, boustrophedonic, curvilinear, or be defined any other suitable geometry.

The pores 111 of the array 110 function to capture and retain cells. Preferably, each pore 111 of the set of pores 112 of the array 110 function to capture and retain a single cell of interest, thus enabling processing and analysis of an individual cell; however, a pore 111 of the set of pores 112 can alternatively be configured to prevent cell capture, or to capture and retain multiple cells. The pores 111 preferably include a chamber 113 configured to receive a cell by a chamber inlet 114 and hold a cell, and a pore channel 117 fluidly connected to the chamber 113 at a chamber outlet 115. The chamber 113 preferably has a length that prevents cell egress due to crossflow within the inlet channel 140, and a width or a depth that prevents excessive cell movement but allows for the cell to move enough such that the cell does not block the pore-inlet channel junction. Preferably, each chamber is physically coextensive with an adjacent chamber by a barrier configured to substantially block fluid flow (e.g., in a direction parallel to fluid flow through the pore channel 117, in a direction perpendicular to fluid flow through the inlet channel 140); however, in alterative configurations, a region between two or more chambers 113 can be configured to permit fluid flow therethrough, and/or may not be physically coextensive with an adjacent pore. The end of the pore channel 117 proximal the chamber outlet 115 preferably has a width that prevents a captured cell of interest 10 from passing through the pore channel 117 to the outlet channel 150, while permitting one or more smaller sample components (e.g. lysed cells, cellular components, undesired fluid components, etc.) to flow therethrough. The end of the pore channel 117 proximal the chamber outlet 115 is preferably smaller than the diameter of a captured cell of interest 10, but can have any other suitable dimension.

The array 110 preferably includes multiple pores 111. For example, an array 110 can include 100, 1000, 10,000, 1,000,000, or any suitable number of pores 220. The pores 111 are preferably fluidly coupled in parallel within the array 110, wherein the longitudinal axes (i.e., a longitudinal axis of symmetry through the chamber inlet, the chamber outlet, and the pore channel) of adjacent pores 220 are preferably parallel and evenly spaced. In some variations of the array with parallel pores 111, however, the pores 220 can be arranged at an angle to adjacent pores 220 within the array 110. In alternative variations, the pores 111 can alternatively be fluidly coupled in any other suitable configuration within the array (e.g., one or more of the pores can be coupled in series, such that a pore channel is fluidly coupled to a chamber inlet of a downstream pore). The pores 111 of an array 110 are preferably substantially similar or identical, with chambers 113 of substantially the same dimension and pore channels 117 of substantially the same dimension. However, an array 110 can have pores 111 with substantially different chamber 113 and pore channel 117 dimensions, with varying chamber 113 lengths, chamber 113 widths, chamber 113 depths, pore channel 117 lengths, pore channel 117 widths, pore channel 117 depths, number of pore channels 117 per pore 111, number of chambers 113 per pore 111, or pores 111 that vary along any other suitable parameter. For example, an array 110 can have multiple pores 111 arranged in parallel, wherein consecutive pores 111 have decreasing pore channel widths (i.e., an upstream pore has a larger dimension than a downstream pore).

The chamber 113 of a pore 111 functions to retain a cell of interest, while allowing undesired sample components to flow through or around the chamber 113. As such, the chamber 113 is preferably fluidly coupled to the inlet channel 140 and the pore channel 117, which is fluidly coupled to the outlet channel 150. The chamber 113 of a pore 111 can also enable retention and eventual transfer of intracellular components (e.g., macromolecules, fragments, nucleic acids, proteins) from a pore channel, for instance, during electrophoresis, after a cell captured within the chamber has been lysed. In one variation, as described in the method 200 below, a cell of interest can be captured within a chamber 113, encapsulated in an encapsulation matrix to further prevent cell egress, lysed by diffusion of a lysing reagent across the encapsulation matrix, and genetic content of the lysed cell can amplified with amplification reagents (e.g., for whole genome amplification), which can enable electrophoretic separation and analysis. However, the chamber 113 can alternatively be configured to capture a desired particle of interest from a sample for any other suitable application.

Figure 2A:
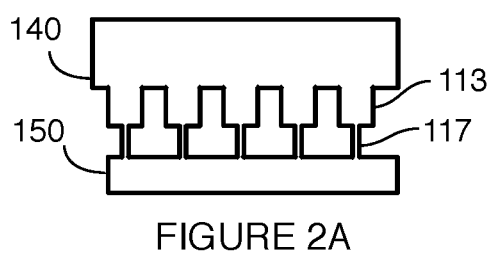
FIGS. 2A, 2B, 2C, 2D, and 2E are schematic representations of a first, second, third, fourth, and fifth pore variation, respectively.
Figure 2B:
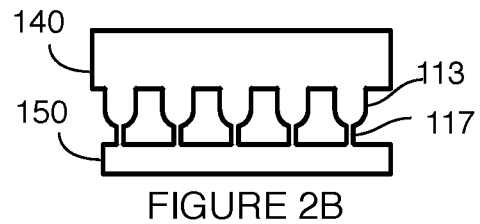
Figure 2C:
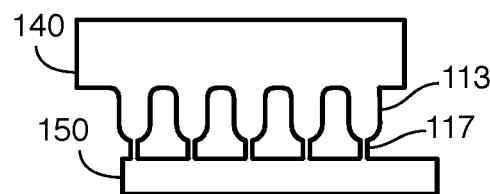
Figure 2D:
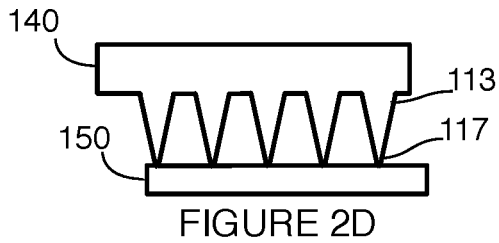
Figure 2E:
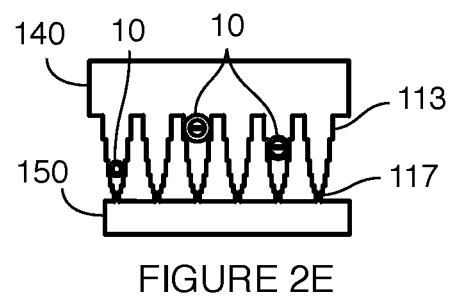

The chamber 113 preferably has a length and width configured to retain an isolated cell, wherein the chamber 113 is dimensioned to prevent cell egress from the chamber 113 due to inlet channel cross-flow. In one variation, this is achieved by controlling the width to height ratio of chamber 113. The width to height ratio of the chamber 222 is preferably 1 (e.g., in order to accommodate an approximately spherical cell), but can alternatively be 1.25, 0.5, or any other suitable ratio. The chamber 113 is preferably configured to retain a single cell and to prevent multiple cell retention. In one variation, the chamber 222 is dimensioned such that the height/width of the chamber 222 prevents a second cell from settling toward the chamber outlet 115 proximal the pore channel 117, and the length of the chamber 222 prevents a single cell egress from the chamber 222 (e.g. the length is longer than the cell diameter), but encourages egress of a second cell from the chamber 222 (e.g. the length is longer than the cell diameter, but shorter than two cell diameters). However, the chamber 222 can be configured to retain multiple cells. The chamber 113 preferably has a length, width and depth each from 5-200 microns, but can alternatively have any other suitable dimensions. In one variation, the chamber has a length of 30 micrometers, a width of 30 micrometers, and a height of 30 micrometers. In another variation, the chamber has a length of 25 micrometers, a width of 25 micrometers, and a height of 30 micrometers. The chamber 113 preferably has a substantially constant cross-section, but can alternatively have a tapering cross-section, preferably that is wider at the chamber inlet 114 and narrower at the chamber outlet 115. The variable cross-section can be the cross-section parallel to the broad face of the substrate 120 and/or the cross-section perpendicular to the longitudinal axis of the chamber 113. In one variation, as shown in FIG. 2A, the chamber 113 has a rectangular cross-section, wherein the pore channel 117 is coupled to the chamber outlet 115, which opposes the chamber inlet 114 coupled to the inlet channel 140. In another variation, the chamber 113 has a parabolic cross section, as shown in FIG. 2B and FIG. 2C, wherein the pore channel 117 connects to the apex of the parabolic profile of the chamber 113 at the chamber outlet 115. In another variation, as shown in FIG. 2D, the chamber cross section linearly decreases from the inlet channel 140 to the pore channel 117. In another variation, as shown in FIG. 2E, the chamber cross-section decreases stepwise from the inlet channel 140 to the pore channel 117. In this variation, the chamber 113 defines multiple sub-chambers, wherein the multiple sub-chambers are preferably fluidly connected in series, wherein a first sub-chamber is fluidly connected to the inlet channel 140 and the last sub-chamber is fluidly connected to the pore channel 117. The first sub-chamber preferably has the largest width and/or depth, and the last sub-chamber preferably has the smallest width and/or depth. The transition between the inlet channel 140 and the chamber 113 preferably exhibits a convex angle (e.g. a 90° angle), but can alternatively be curvilinear as shown in FIG. 2C, or defined by any other suitable path. The transition between the chamber 113 and the pore channel 117 preferably also exhibits a convex angle (e.g. a 90° angle), but can alternatively be curvilinear or defined by any other suitable path.

The pore channel 117 of the pore 113 functions to enable retention of a captured cell of interest 10 and to allow smaller sample components to flow through. The pore channel 117 is preferably fluidly connected to the chamber outlet 115 and the outlet channel 150. The pore channel 117 is preferably substantially straight and linear, but can alternatively be curvilinear or be defined by any other suitable geometry. The pore channel 117 preferably has a width smaller than the diameter of the cell of interest 10, such that the pore channel 117 prevents passage of a cell of interest therethrough. The pore channel 117 preferably has a width and depth from 1-25 microns and a length from 5-500 microns, but can have any other suitable width, depth, and/or length. In one variation, the pore channel 117 has a width of 7-10 micrometers, a depth of 7-10 micrometers, and a length of 5-50 micrometers. The pore channel 117 preferably has a substantially constant cross-section, and in a specific example, the pore channel 117 has a cross section of 8 micrometers×10 micrometers. However, the pore channel 117 can alternatively have a tapering or variable cross section. In one such variation, the pore channel 117 can be wider proximal the chamber outlet 115 and narrow proximal the outlet channel 150. The pore channel 117 is preferably aligned with its longitudinal axis parallel with the longitudinal axis of the chamber 113. More preferably, the pore channel 117 is coaxial with the chamber 113. However, the pore channel 117 can be aligned at an angle with the chamber 113 or have any other suitable configuration relative to the chamber 113. Each pore 111 preferably includes a single pore channel 117, but can alternatively include multiple pore channels 117, wherein the multiple pore channels 117 preferably extend in parallel from the end of the respective chamber 113 proximal the outlet channel 150.

1.2 System—Inlet and Outlet Channels

Figure 3:
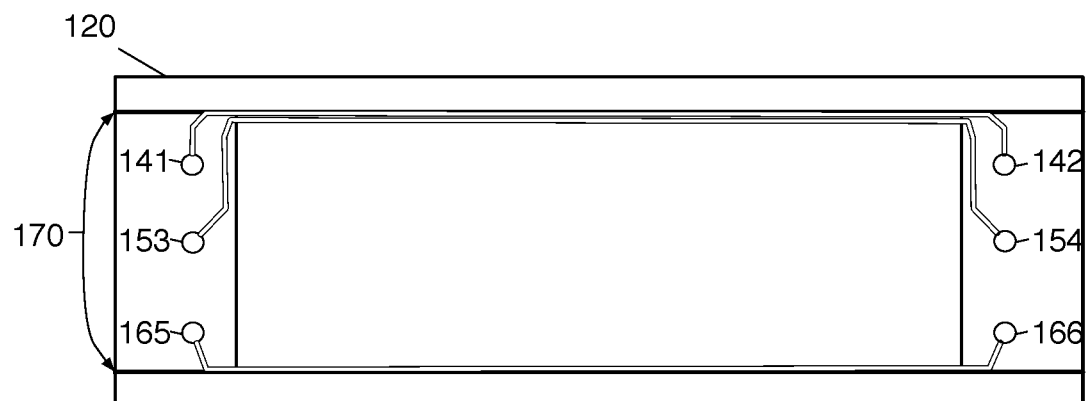
FIG. 3 is a top view of a variation of the system.

The inlet channel 140, as shown in FIG. 1B, functions to receive a volume of a biological sample and to distribute the biological sample to the set of pores 112. In variations of the system 100 that allow for electrophoretic analysis of a set of particles, the inlet channel 140 can additionally or alternatively function to receive and facilitate distribution of a phase-changing matrix (e.g., gel) that allows encapsulation of captured cells of interest at the pores 111. The inlet channel 140 preferably includes a first end, a second end, and a channel connecting the first and second ends. The inlet channel 140 is preferably coupled to a first port 141 at the first end, is fluidly connected to the chambers 113 of the array 110 along the inlet channel 140 length, and is preferably coupled to a second port 142 at the second end, as shown in FIGS. 1C and 3. The inlet channel 140 preferably includes a first and/or second valve disposed within the first and/or second end (e.g., proximal the first port 141, proximal the second port 142), wherein the valves can operate between an open and a closed state, in order to facilitate guidance of sample, reagent, and/or encapsulation matrix flow. In some variations, the first port 141 can facilitate reception of the biological sample and a matrix for encapsulation of elements captured in the pores 111, and the second port can facilitate displacement of the matrix for encapsulation, prior to gelation or solidification, in order to form a channel that allows for reagent diffusion across the matrix. In some variations, however, any of the first end and the second end can be sealed by the substrate 120 or can be sealed by a sealant, such as a self-sealing laminate (e.g. made of rubber, polyethylene, etc.). The body of the inlet channel 140 is preferably defined by the substrate 120, but can alternatively be partially defined by the substrate 120, wherein the other portions can be defined by self-sealing laminate or any other suitable sealant.

The inlet channel 140 is preferably arranged such that a longitudinal axis of the inlet channel 140 is perpendicular to the longitudinal axes of the chambers 113; however, the inlet channel 140 can alternatively be arranged at an angle relative to the chambers. The chambers 113 preferably extend from a single side of the inlet channel 140, but can alternatively extend from multiple sides (e.g. opposing sides) of the inlet channel 140. The inlet channel 140 is preferably substantially straight, but can alternatively be curved, bent, or defined by any other suitable geometry. The inlet channel 140 preferably has a substantially constant rectangular cross-section, but can alternatively have a variable cross section (e.g., a cross-section parallel to the inlet channel longitudinal axis and/or a cross-section perpendicular to the inlet channel longitudinal axis can be constant or variable) that is defined by any other suitable geometry (e.g., polygonal, curvilinear). In one variation, the inlet channel 140 tapers with distance away from the first port 141. The inlet channel 140 preferably has a depth and width larger than the diameter of the cell of interest 10, such that cells of interest can flow freely through the inlet channel 140 without undergoing deformation; however, the inlet channel can be dimensioned relative to a cell of interest in any other suitable manner. The inlet channel 140 preferably a depth and/or width between 5-200 microns, but can alternatively have any suitable depth and/or width. In one variation, the inlet channel has a width of 70-100 micrometers, and a depth of 50-100 micrometers, and in a specific example, the inlet channel 140 has a cross sectional dimensions of 100 micrometers by 100 micrometers. The inlet channel 140 preferably has a length that can accommodate all the pores 111 of the array 110; however, in some variations, the inlet channel 140 can feed a portion of the set of pores 112, and not directly be coupled to remaining pores of the set of pores 112. In one variation, the inlet channel 140 preferably has a length longer than the combined widths of the chambers 113, such that the chambers 113 are spaced apart from each other (e.g., with uniform or non-uniform barriers to fluid flow). In another variation, the inlet channel 140 extends to the edge of the substrate 120. However, the array 110 can include any suitable configuration of inlet channels 240.

The outlet channel 150, as shown in FIG. 1C, functions to receive and transmit undesired components of a volume of a biological sample passed through the inlet channel 140 and transmitted through the set of pores 112. As such, the outlet channel 150 can allow transmission of "waste" fluid from the substrate 120, and/or transmission of biological sample components, omitting the cells of interest, for further processing and analysis. In variations of the system 100 allowing for electrophoretic analysis of particles, the outlet channel 150 can additionally or alternatively facilitate transfer of excess encapsulation matrix and/or sieving matrix from the substrate 120, and can additionally or alternatively facilitate transfer and distribution of a sieving matrix for electrophoresis. The outlet channel 150 preferably includes a first end, a second end, and a channel connecting the first and second ends. The outlet channel 150 is preferably coupled to a third port 173 at the first end, is fluidly connected to the pore channels 117 of the array 110 along the outlet channel 150 length, and is preferably coupled to a fourth port 174 at the second end of the outlet channel 150, as shown in FIGS. 1C and 3. The outlet channel 150 preferably includes a first and/or second valve disposed within the first and/or second end (e.g., proximal the third port 173, proximal the fourth port 174) of the outlet channel 150, wherein the valves can operate between an open and a closed state, in order to facilitate guidance of sample waste, excess reagent, and/or excess sieving matrix flow. In some variations, the third port 173 can facilitate reception of a sieving matrix for electrophoresis, and the fourth port 174 can facilitate transfer of excess reagents, waste, undesired sample components, and/or any other suitable type of matter from the substrate 120. In other variations, however, the first end of the outlet channel 150 and/or the second end of the outlet channel 150 can be sealed by the substrate 120 or can be sealed by a sealant, such as a self-sealing laminate (e.g. made of rubber, polyethylene, etc.). Similar to the inlet channel 140, the body of the outlet channel 150 is preferably defined by the substrate 120, but can alternatively be partially defined by the substrate 120, wherein the other portions can be defined by self-sealing laminate or any other suitable sealant.

The outlet channel 150 is preferably arranged such that a longitudinal axis of the outlet channel 150 is perpendicular to the longitudinal axes of the chambers 113; however, the outlet channel 150 can alternatively be arranged at an angle relative to the chambers 113 of the array 110. Similar to the inlet channel 140, the chambers 113 preferably extend from a single side of the outlet channel 150, but can alternatively extend from multiple sides (e.g. opposing sides) of the outlet channel 150. The outlet channel 150 is preferably substantially straight, but can alternatively be curved or bent, or defined by any other suitable geometry. The outlet channel 150 preferably has a substantially constant rectangular cross-section, but can alternatively have a variable cross section (e.g., the cross-section parallel the outlet channel longitudinal axis and/or the cross-section perpendicular the outlet channel longitudinal axis can be constant or variable) that is defined by any other suitable geometry (e.g., polygonal, curvilinear). In one variation, the outlet channel 150 tapers with distance away from the outlet third port 153. The outlet channel 150 preferably has a depth and width similar to that of the inlet channel 140, but can alternatively have a depth and width smaller or larger than that of the inlet channel 140. The outlet channel 150 preferably a depth and/or width between 5-200 microns, but can alternatively have any suitable depth and/or width. In one variation, the outlet channel has a width of 50-100 micrometers, and a depth of 50-100 micrometers, and in a specific example, the outlet channel 150 has cross sectional dimensions of 100 micrometers by 100 micrometers. The outlet channel 150 preferably has a length that can accommodate all the pores 220 of the array 110. In one variation, the outlet channel 150 preferably has a length longer than the combined widths of the chambers 113, such that the chambers 113 are spaced apart by barriers to fluid flow. In another variation, the outlet channel 150 extends to the edge of the substrate 120.

In some variations, the system 100 can further include at least one of an inlet manifold configured to couple to the inlet channel 140 (e.g., at one of the first port 141 and the second port 142) and an outlet manifold configured to couple to the outlet channel 150 (e.g., at one of the third port 173 and the fourth port 174). The inlet manifold functions to receive a volume of a biological sample and to distribute the sample to the arrays 200, and the outlet manifold functions to facilitate transfer of undesired biological sample components and/or excess matrices for encapsulation/electrophoresis from the substrate 120. The inlet manifold and/or the outlet manifold can be that described in U.S. Pub. No. 2013/0190212, entitled "Cell Capture System and Method of Use" filed 25 Jul. 2012, which is incorporated herein in its entirety by this reference; however, the inlet manifold and/or the outlet manifold can alternatively be any other suitable inlet manifold/outlet manifold.

1.3 System—Electrophoresis

Figure 4:
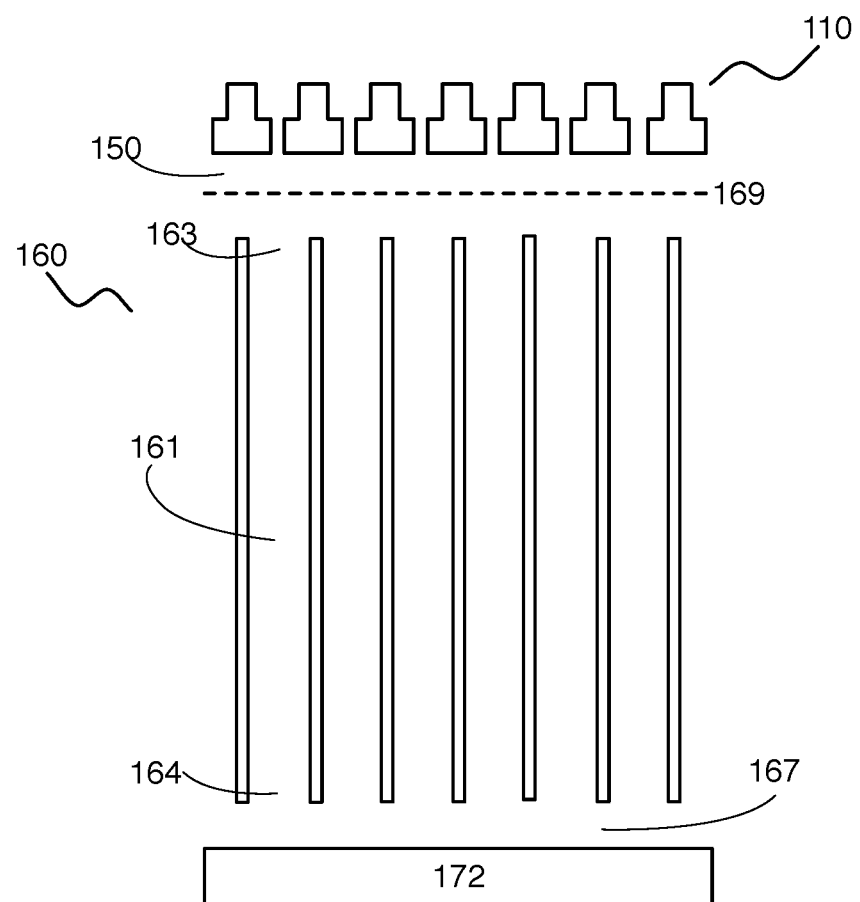
FIG. 4 is a top view schematic of a portion of a variation of the system.

As shown in FIGS. 1B and 4, the system 100 can further include a set of electrophoresis channels. The set of electrophoresis channels function to receive a sieving matrix and facilitate electrophoretic separation of processed intracellular content from the cells of interest captured at the set of pores 112 of the array 110. The set of electrophoresis channels 160 is preferably fluidly coupled to the pore channels 117 of the array 110 by the outlet channel 150; however, the set of electrophoresis channels 160 can be fluidly coupled to the pore channels 117 in any other suitable manner. Preferably, each electrophoresis channel 161 of the set of electrophoresis channels 160 is paired with a pore 111 of the set of pores 112, in a one-to-one manner; as such, each pore channel 117 of the array 110 is preferably aligned with a corresponding electrophoresis channel 161 of the set of electrophoresis channels 160, in order to facilitate electrophoretic separation along a linear path. In specific examples, the system 100 can include 100, 1,000, 10,000, 1,000,000, or any suitable number of electrophoresis channels 161 to match the number of pore channels 117 in the array. However, the set of electrophoresis channels 160 can be configured relative to the pore channels 117 of the array 110 in a manner that is not one-to-one (e.g., contents of multiple pore channels can feed into a single electrophoresis channel, an electrophoresis channel can be sufficiently wide to span multiple pore channels, etc.), in a manner wherein the electrophoresis channels 160 are not aligned with the pore channels 117, along a non-linear path, and/or in any other suitable manner.

As shown in FIG. 1B, each electrophoresis channel 161 in the set of electrophoresis channels 160 preferably includes an electrophoresis inlet 163 proximal the outlet channel 150 and aligned with a pore channel 117, and an electrophoresis outlet 164. The electrophoresis inlets 163 can be partially separated from the outlet channel 150 by a porous membrane 169, as shown in FIG. 1B, configured to block a majority of fluid flow from the outlet channel (e.g., such that a majority of the fluid flows out of the fourth port 174 without entering the electrophoresis inlets 163), but that still allows a conductive interface to form between an encapsulation matrix and a sieving matrix delivered into the substrate 120. However, the electrophoresis inlets 163 and the outlet channel 150 can be separated in any other suitable manner, and/or not separated by a membrane. The electrophoresis inlet 163 functions to receive processed intracellular components that are electrokinetically driven by an electric field, and the electrophoresis outlet 164 functions to facilitate distribution of a sieving matrix for electrophoresis, such that intracellular macromolecules and fragments (e.g., proteins, nucleic acids) can be separated along an entire length of an electrophoresis channel 161. The length of the electrophoresis channel 161 thus preferably defines a length that allows for separation of macromolecules and fragments with proper resolution (e.g., clear separation of bands characterizing specific macromolecules and fragments), and in one variation, is minimized to contribute to compactness of the system 100. However, in other variations, the length of an electrophoresis channel 161 can be any other suitable length (e.g., not minimized), for example, in applications wherein compactness is less of a concern. As such, a region between each electrophoresis inlet 163 and electrophoresis outlet 164 functions to provide a pathway along which intracellular macromolecules and fragments can be separated and analyzed with suitable band resolution. Preferably, the cross-section of an electrophoresis channel 161 defines a rectangular geometry with a low aspect ratio; however, an electrophoresis channel 161 can alternatively have any other suitable cross-sectional geometry defining any other suitable aspect ratio.

Each electrophoresis channel 161 is preferably defined within the substrate 120 using techniques identical to that of forming at least one of the array 110, the inlet channel 140, and the outlet channel 150, such that processing of the set of electrophoresis channels 160 can be performed simultaneously with at least one of the array 110, the inlet channel 140, and the outlet channel 150. However, the set of electrophoresis channels 160 can be performed in any other suitable manner. In one specific example, the electrophoresis channels 161 are processed simultaneously with the array 110, the inlet channel 140, and the outlet channel, using a three mask photolithographic process and deep reactive ion etching (DRIE) process to etch the set of electrophoresis channels 160 into a silicon or glass substrate as a mold. In the specific example, the etched elements are then transferred to 1 millimeter thick polymethylmethacrylate (PMMA) sheets as a substrate 120 using a hot embossing process, which is then laminated with a polymethylmethacrylate (PMMA) laminate to define the set of electrophoresis channels 160. In the specific example, lamination includes utilizing an appropriate roller speed, temperature, pressure, and tension of the laminate to ensure a low level of ingress of laminate material into microfluidic structures. The chamber 113 preferably has a width and depth each from 5-200 microns, but can alternatively have any other suitable dimensions. In a specific example, each electrophoresis channel 161 has a length of approximately 15 millimeters, a width of 30 micrometers, and a depth of 8 micrometers. As such, the specific example of the set of electrophoresis channels 160 provides channels for electrophoretic separation with a length for suitable band resolution, and a cross-section with a low aspect ratio that facilitates visualization of bands.

As shown in FIG. 4, each electrophoresis outlet 164 of the set of electrophoresis channels 160 is preferably fluidly coupled to an electrophoresis outlet channel 167, which functions to facilitate distribution of a sieving matrix throughout the set of electrophoresis channels 160 for electrophoresis, and facilitate distribution of reagents (e.g., separation buffer) throughout the system 100 for processing of the set of cells. The electrophoresis outlet channel 167 preferably includes a first end, a second end, and a channel connecting the first and second ends. The electrophoresis outlet channel 167 is preferably coupled to a fifth port 167 at the first end, is fluidly connected to the electrophoresis outlets 164 of the set of electrophoresis channels 160 along the electrophoresis outlet channel 167 length, and is preferably coupled to a sixth port 166 at the second end of the electrophoresis outlet channel 167, as shown in FIG. 1B. The electrophoresis outlet channel 167 preferably includes a first and/or second valve disposed within the first and/or second end (e.g., proximal the fifth port 167, proximal the sixth port 166) of the electrophoresis outlet channel 167, wherein the valves can operate between an open and a closed state, in order to facilitate guidance of excess reagent and/or excess sieving matrix flow. In some variations, the fifth port 167 can facilitate reception of a buffer (e.g., a separation buffer) that is transferred throughout the sieving matrix for electrophoresis, and the sixth port 166 can facilitate transfer of excess reagents, excess sieving matrix and/or any other suitable type of matter from the substrate 120. In relation to the inlet channel 140, the outlet channel 150, and the electrophoresis outlet channel 167, any one or more of the first port 141, the second port 142, the third port 153, the fourth port 154, the fifth port 165, and the sixth port 166 can facilitate reception of a buffer (e.g., a separation buffer) that is transferred throughout the sieving matrix for electrophoresis. Furthermore, the system 100 can include any other suitable number of ports (e.g., coupled to the inlet channel, coupled to the outlet channel, coupled to the electrophoresis outlet channel, defined within any other suitable location of the substrate) configured to facilitate processing of the set of cells. In other variations, however, the first end of the outlet channel 150 and/or the second end of the electrophoresis outlet channel 167 can be sealed by the substrate 120 or can be sealed by a sealant, such as a self-sealing laminate (e.g. made of rubber, polyethylene, etc.). Similar to the inlet channel 140 and the outlet channel 150, the body of the electrophoresis outlet channel 167 is preferably defined by the substrate 120, but can alternatively be partially defined by the substrate 120, wherein the other portions can be defined by self-sealing laminate or any other suitable sealant.

Also shown in FIG. 1B, the system 100 can further include a set of electrodes 170. The set of electrodes 170 function to provide an electric field across the substrate 120 in a manner that facilitates electrokinetic movement of processed intracellular content from the cells of interest captured at the set of pores 112 of the array 110, through the set of electrophoresis channels 160. Preferably the set of electrodes includes a first electrode 171 configured to provide a positive voltage and a second electrode 172 configured to provide a negative voltage, such that an electric field is created between the first electrode 171 and the second electrode 172, as shown in FIGS. 1B and 4. Preferably, the first electrode 171 is configured proximal to a location upstream of the set of pores, and the second electrode 172 is configured proximal to a location downstream of the set of electrophoresis channels. In one variation, the first electrode 171 is coupled to the substrate 120 proximal the inlet channel 140, and the second electrode 172 is coupled to the substrate 120 proximal the electrophoresis outlet channel 167 and the electrophoresis outlets 164 of the set of electrophoresis channels 160, such that intracellular macromolecules and fragments can be electrokinetically driven from the chambers 113 of the array 110, through the pore channels 117, and through the set of electrophoresis channels 160 in an electrophoresis inlet-to-electrophoresis outlet direction. In another variation, the first electrode 171 can be coupled to the substrate 120 proximal the chambers 113 of the array, and in yet another variation, the first electrode 171 and the second electrode 172 can be coupled to the substrate at opposing peripheral regions of the substrate 120; however, in other variations, the set of electrodes 170 can be configured in any other suitable manner relative to the substrate.

The set of electrodes 170 preferably includes electrically conductive elements that can be coupled to a source configured to generate specified voltages. In variations, the electrically conductive elements can include any one or more of: composite materials, alloys, pure materials, and any other suitable electrically conductive material. Furthermore, the electrically conductive elements are preferably wires; however, the electrically conductive elements can alternatively be defined by any other suitable form factor (e.g., particulate, sheet, etc.). The set of electrodes 170 can be coupled to the substrate using any suitable process, and in variations, can be coupled using any one or more of: lamination, a thermal bonding method, and adhesives to provide robust coupling. In a specific example, the set of electrodes 170 includes gold-coated copper wires that are 0.1 millimeters in diameter, which are laminated between the PMMA substrate 120 and the PMMA laminate proximal the inlet channel 140 and the electrophoresis outlet channel 167, with electrically conductive epoxy that provides electrical contacts for microelectrophoresis. However, the set of electrodes 170 can include any other suitable number of electrodes, and can be configured relative to the system 100 in any other suitable manner.

1.4 System—Additional Elements

Figure 5A:
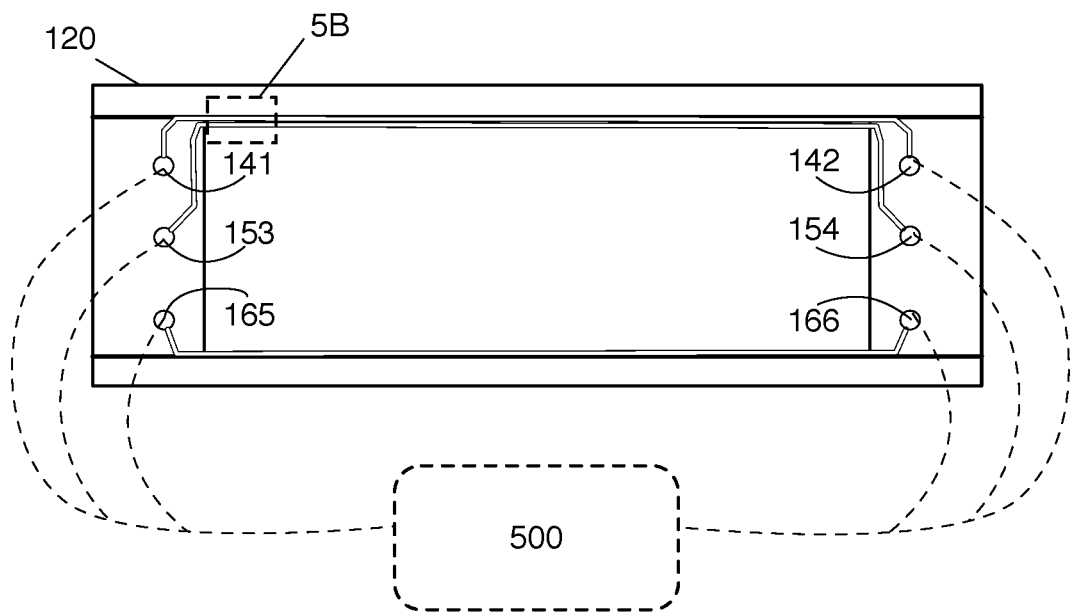
Figure 5B:
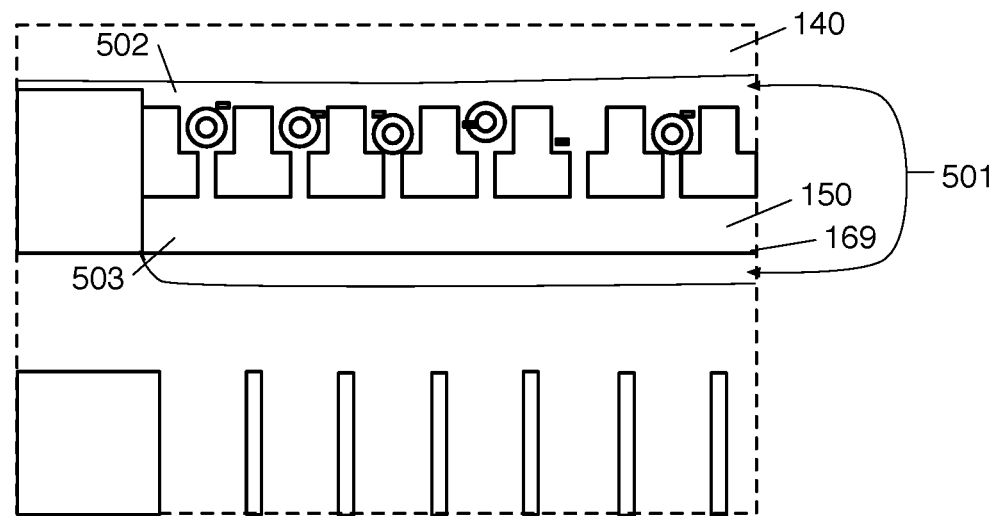

As shown in FIGS. 5A and 5B, the system 100 can additionally include an encapsulation module 500 that functions to encapsulate cells and/or other captured particles (e.g., reagent particles) within individual pores 111. In one variation, the encapsulation module 500 can implement any one or more of the first port 141, the second port 142, the third port 153, the fourth port 154, the fifth port 165, and the sixth port 166, in order to isolate particles at the pores 111 of the array 110. In one variation, an encapsulation matrix 501 can be flowed through the first port 141, into the inlet channel 140, through the pores 111, and out of the outlet channel 150 to the fourth port 154, forming a first encapsulation layer 502 between the set of pores 112 and the inlet channel 140, and a second encapsulation layer 503 between the pore channels 117 of the array 110 and the outlet channel 150. The encapsulation layers are preferably 10 to 20 micrometers thick, but can alternatively be thicker or thinner. During encapsulation matrix introduction, buffer is preferably simultaneously flowed through the inlet channel 140 and outlet channel 150, preferably in the same direction as encapsulation matrix flow, wherein the buffer flow rate preferably controls the thickness of the encapsulation matrix layers 502, 503. Buffer flow is preferably established in the portions of the inlet channel 140 and outlet channel 150 distal from the pores 220. The buffer flow rate is preferably maintained at laminar flow, but can alternatively have any other suitable flow rate. However, any other suitable mechanism that can establish a first and second encapsulation layer can be used.

Figure 5C:
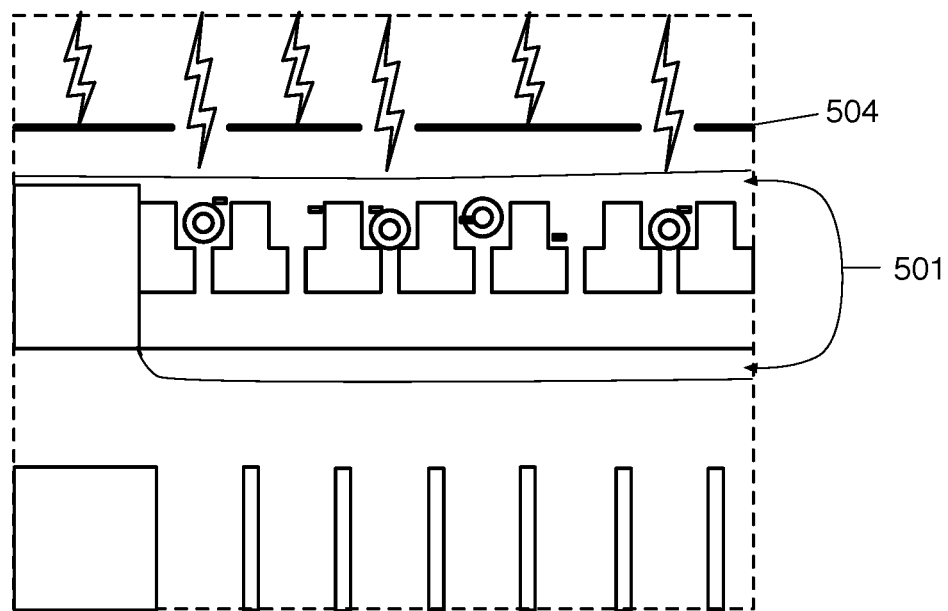

The encapsulation matrix 501 preferably isolates a pore 117 within an array 110. The encapsulation matrix 501 preferably has a flow state and a set state, wherein a photochemical reaction, phase transition, thermochemical reaction, polymerization reaction or any other suitable reaction switches the encapsulation matrix from the flow state to the set state. In the flow state, the encapsulation matrix 501 is preferably substantially viscous, such that the encapsulation matrix 501 does not flow into the pores 111 during introduction into the system 100. In the set state, the encapsulation matrix 501 is preferably a solid or gel that prevents particle egress from the pores 111 (e.g., egress of cells and large nucleic acid molecules from the pores), and is preferably porous or selectively permeable to permit small molecule, buffer, and reagent penetration therethrough. In one variation, the encapsulation matrix 501 is a microporous agarose gel, and in another variation, the encapsulation matrix is a photopolymerizable hydrogel, such as PEG or polyacrylamide with photoinitiator; however, the encapsulation matrix can alternatively be any suitable material with any other suitable polymerization agent. In some variations, select portions of the encapsulation matrix 501 can be reacted to seal specific pores 111. For example, as shown in FIG. 5C, a unique photomask 504 can be created that allows collimated irradiation of encapsulation matrix segments blocking pores 111 containing the cells of interest, while leaving pores void of cells of interest not encapsulated. The photomask 504 can be created by high resolution printing of UV-blocking black ink on a transparency sheet or by use of standard photolithography on photoresist coated glass masks. The selective UV exposure of select regions of the microfluidic chip can also be accomplished by moving a UV laser or a collimated and concentrated UV spot to the select locations using an x-y stage. Undesired sample components 20 and unreacted encapsulation matrix 501 can then be removed from the system 100 by ingressing fluid through the outlet channel 150 (e.g. backflowing) and/or the inlet channel 140. Alternatively, the photomask 504 can allow irradiation of encapsulation matrix segments blocking pores 111 containing undesired sample components 20, wherein desired cells 10 are retrieved from the system. However, any suitable portion of the encapsulation matrix 501 can be reacted. In one alternative variation, a molten encapsulant can be flown into desired portions (e.g., a portion or all the microfluidic network), and the molten encapsulant can be transitioned to a set-stage. In the alternative variation, an irradiation device (e.g., an infrared laser) can then be used to irradiate desired regions of the microfluidic network to melt desired sections and create a desired flow path.

Figure 6:
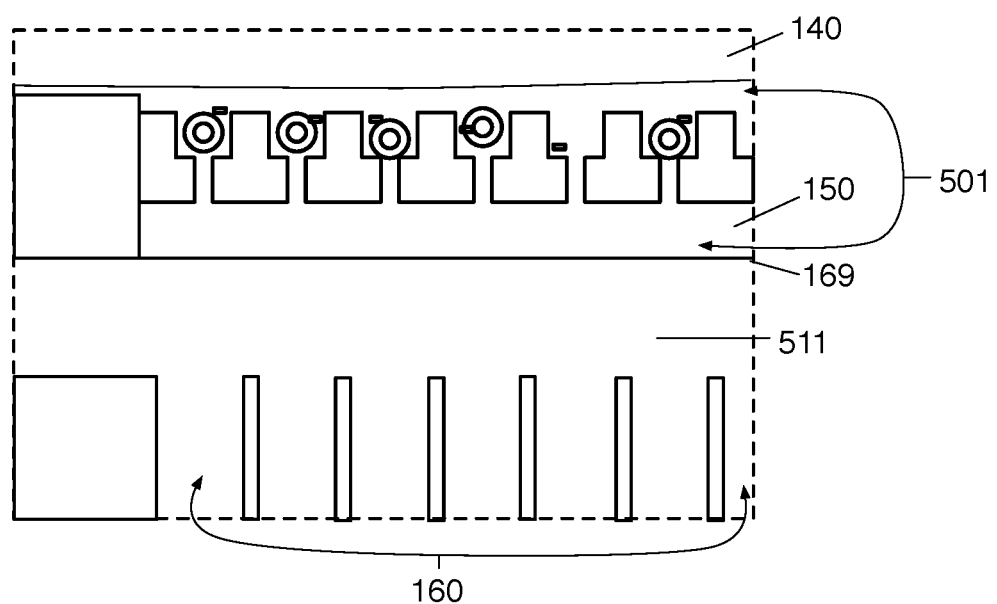
FIG. 6 depicts a schematic of a portion of an embodiment of the system.

In some variations, as shown in FIGS. 5A and 6, the encapsulation module 500 can further facilitate distribution of a sieving matrix 511 throughout the system 100 (e.g., the set of electrophoresis channels 160), in order to provide a continuous matrix that allows for separation and analysis of intracellular components by electrophoresis. The sieving matrix 511 can be identical in composition to the encapsulation matrix 501, or can be non-identical in composition to the encapsulation matrix 501. Preferably, the sieving matrix 511 is configured to provide a continuous interface with the encapsulation layers formed by the encapsulation matrix 501; however, the sieving matrix 511 can alternatively be configured in any other suitable manner. In one example, the encapsulation module 500 can utilize the third port 153 and the sixth port 166, in distributing a sieving matrix across the set of electrophoresis channels 160; however, other variations can use any other suitable port for transferring sieving matrix into the system 100.

Figure 7A:
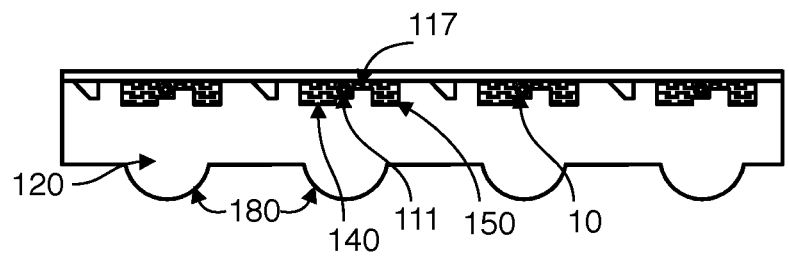
FIGS. 7A, 7B, and 7C depict variations of an encapsulation module of an embodiment of the system.
Figure 7B:
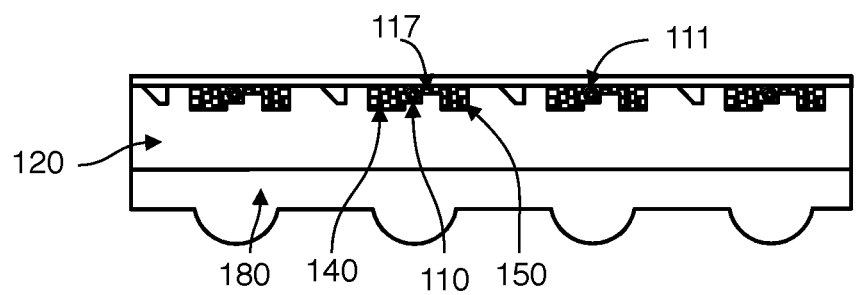
Figure 7C:
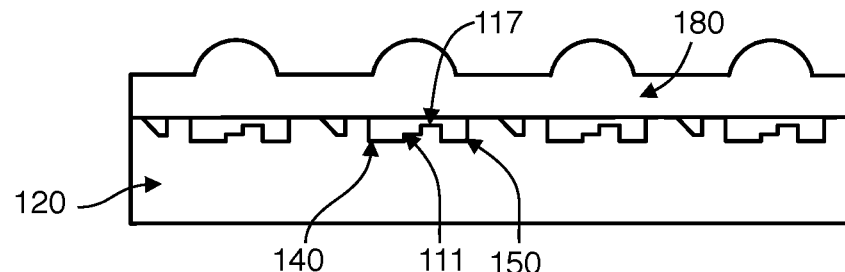
Figure 7D:
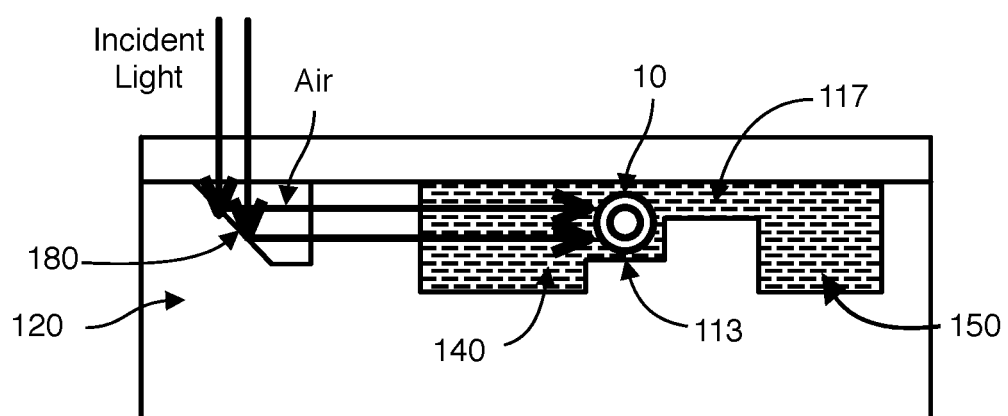

The system 100 can additionally include optical elements 180 that function to facilitate imaging. The optical elements 180 function to adjust incoming light, preferably to facilitate better imaging. The optical elements 180 can function to bend, reflect, collimate, focus, reject, or otherwise adjust the incoming light. The optical elements 180 are preferably fabricated within the same process as the system 100 manufacture, but can alternatively be included after system 100 manufacture. The optical elements 180 are preferably defined within the substrate 120, but can alternatively be defined by any other suitable component of the system 100. Optical elements 180 can include light reflectors disposed within the substrate thickness adjacent the array(s) 110 (as shown in FIG. 7A), defined on a broad face of the substrate 120 opposite that defining the array 110 (as shown in FIG. 7B), or microlenses defined on a broad face of the substrate proximal that defining the array 110 (as shown in FIG. 7C), light collimators, light polarizers, interference filters, 90° illumination, elements that minimize excitation rays from going into path of collected fluorescence emission light, diffraction filters, light diffusers, or any other suitable optical element. In one such variation, the substrate can further include a reflector, separated from the inlet channel by an air gap and configured to reflect incident light at a 90 degree angle longitudinally into each pore of the set of parallel pores, as shown in FIG. 7D. Alternatively, the optical elements 180 can be defined by an imaging stage or by any external component.

The system 100 can additionally include pore affinity mechanisms that function to attract a cell of interest 10 towards a pore 111. Pore affinity mechanisms can include electric field traps, features within the inlet channel 140 that direct flow into a pore 111, negative pressure application to the outlet channel 150, or any other suitable pore affinity mechanism.

Figure 8A:
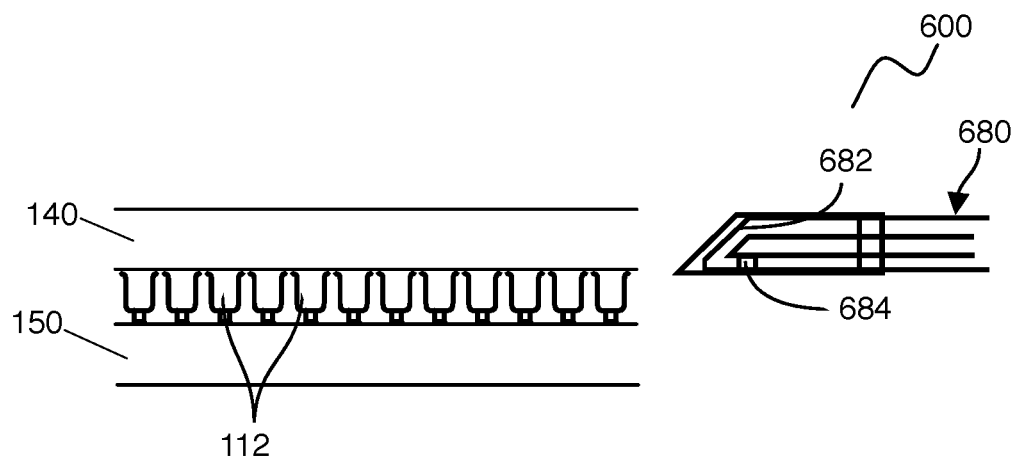
FIGS. 8A, 8B, and 8C are views of a variation of the cell removal tool.
Figure 8B:
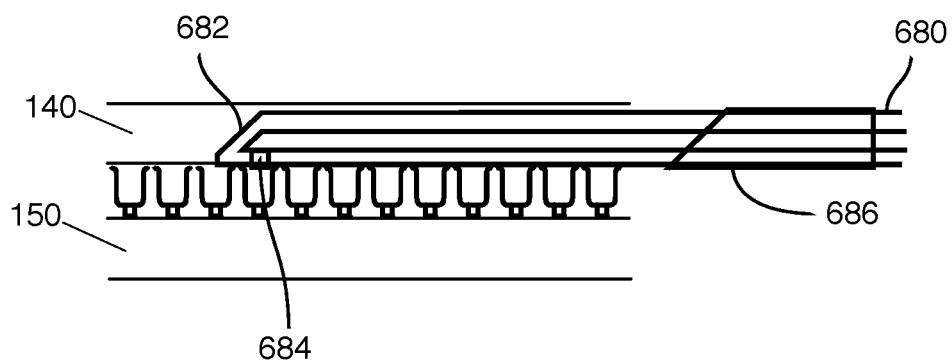

In some variations, the system 100 can further be configured to facilitate selective cell removal from known, addressable locations. While an individual cell from a single pore 111 is preferably selectively removed, the system can facilitate simultaneous removal of multiple cells from a single array 110. The cell is preferably removed by applying a removal force to a cell captured within a chamber 113. The removal force is preferably applied by pumping fluid through the pore channel 117 into the chamber 113, but can alternatively be applied by aspirating the contents out of the chamber 113. In one variation, the pump pressure provided by a pump mechanism at an outlet of the system 100 is less than 10,000 Pa, in order to prevent damage to a cell being retrieved. In one specific variation, the provided pump pressure is 6,000 Pa. However, any other suitable pump or aspiration pressure can be used. In some variations, cell removal can be achieved by utilizing a cell removal tool 600. The cell removal tool 600 of the system 100 functions to selectively remove one or more isolated cells from an addressable location within the system 100. The cell removal tool 600 is preferably configured to remove a cell from a single chamber 113, but can alternatively be configured to simultaneously remove multiple cells from multiple chambers 113. In some variations, the cell removal tool can additionally or alternatively be configured to selectively deliver specific reagents (e.g., cell lysis reagents, nucleic acid binding reagents/particles, biomarker binding or detection reagents, etc.) to select cells and/or can be used to selectively remove cellular components, such as cell lyate, nucleic acid from select cells. In one variation, the cell removal tool 600 is configured to remove one or more cells from the system 100 in a direction substantially parallel to the broad face of the substrate 120. As shown in FIGS. 8A and 8B, the cell removal tool 600 preferably includes a cannula 680 defining a lumen and an aperture 684. The cannula 680 preferably terminates in a sealed puncture tip 682 at a first end, and is preferably fluidly connected to a cell collection volume at a second end. The aperture 684 is preferably a hole that extends through the cannula 680 wall, wherein the hole preferably has a width substantially equivalent to or larger than the width of a pore chamber 222, but small enough such that the aperture 684 does not span two pore chambers 113. The cannula 680 preferably includes one aperture 684, but can alternatively include multiple apertures 684, wherein the multiple apertures 684 can be aligned in a line parallel to the longitudinal axis of the cannula 680, or can be distributed about the surface of the cannula 680 (e.g. spiral about the longitudinal axis of the cannula 680). The aperture 684 preferably extends through a longitudinal cannula 680 wall, but can alternatively extend through a portion of the puncture tip 682. In one example, the aperture 684 extends through a portion of the longitudinal cannula wall proximal the puncture tip 682. In another example, the aperture 684 extends through a portion of the longitudinal cannula wall a predetermined distance from the puncture tip 682, wherein the distance can be configured such that the cannula wall blocks one or more of the adjacent pores 220.

In another example, the aperture 684 can extend through the puncture tip 682 such that the longitudinal axis of the aperture 684 extends in parallel or coaxially with the longitudinal axis of the cannula 680. The transition between the aperture 684 and the cannula 680 exterior and/or interior is preferably convex and curved to prevent cell damage, but can alternatively be concave, angled, be at right angles, or have any suitable configuration. The cannula 680 preferably has a circular cross section, but can alternatively have a rectangular or square cross section, ovular cross section, or any other suitable cross section. The cannula 680 is preferably rigid, but can alternatively be flexible or include flexible portions. In one alternative, the cannula 680 is flexible and includes a rigid puncture device 686, wherein the rigid puncture device 686 is slidably coupled over the cannula 680. The rigid puncture device 686 forms and retains an entryway into the inlet channel 140, and the cannula 680 can be advanced therethrough. However, the cannula 680 can have any other suitable configuration. The cannula 680 can additionally include a perforator slidably coupled within the lumen, wherein the perforator can extend through the aperture 684 to perforate any intermediary layers between the cannula 680 and the pore 111 (e.g. an encapsulation layer). The perforator position post perforation can be retained to facilitate cell removal therethrough, or the perforator can be retracted prior to cell removal.

Figure 8C:
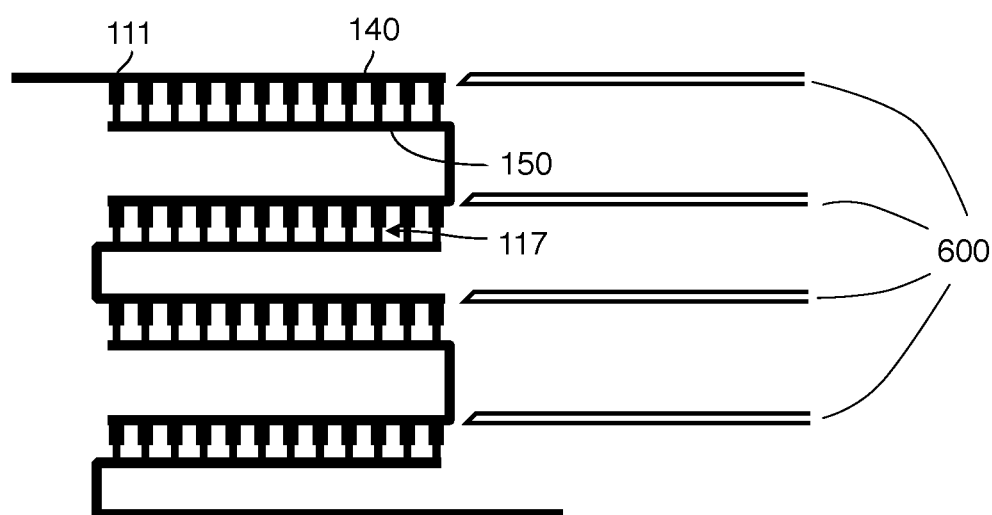

In one variation of cell retrieval tool operation, the cannula preferably traverses through the inlet channel 140 of the array 110 (e.g., through one of the first port 141 and the second port 142, through a side adjacent to or opposing a broad surface of the substrate 120), until the aperture is aligned with the pore 111 containing the cell of interest 10. The inlet channel can thus function as a guide to guide the cell removal tool to a pore, and in variations wherein the system 100 includes arrays coupled in series, inlet channels for different arrays can be configured to guide the cell removal tool for extraction of a captured cell, as shown in FIG. 8C. Fluid can then be ingressed through an outlet manifold coupled to an outlet channel 150 of an array 110, wherein the pressure of the ingressed fluid pushes the cell of interest 10 out of the pore chamber 113, through the aperture 684, and into the cannula. Subsequent fluid ingress through the inlet channel 140 can recapture any cells that were backflowed out of their respective pores 111. The cannula can additionally or alternatively include a low-pressure generation mechanism fluidly coupled to the lumen that aspirates the cell out of the pore 111. Alternatively or additionally, the cannula can facilitate cell ingress through capillary action. The cell preferably travels through the lumen and is stored within the cell collection volume.

In this variation of cell retrieval tool operation, the cannula is preferably inserted into the inlet channel 140 through the side of the substrate 120, as shown in FIG. 8B, wherein the inlet channel 140 preferably partially defined by a self-sealing portion (e.g., a self-sealing wall) that provides a hermetic seal about the cell removal tool upon penetration of the self-sealing portion. One or more inlet channels 140 coupled to an array 110 can further be substantially aligned with a guide 650 that facilitates guidance of the cell removal tool 600 into a respective inlet channel 140 for retrieval of a captured cell 10, wherein the guide 650 is separated from a respective inlet channel 140 by the self-sealing portion. The cannula is preferably extended through this self-sealing portion in order to access a captured cell of interest. Alternatively, the cannula can be inserted into the inlet channel 140 through a top layer of the substrate 120, wherein the cannula can be flexible to accommodate the angle of entry, or the top layer can be elastic to accommodate the angle of entry. However, any other suitable method of introducing the cannula into the inlet channel 140 can be used, and introduction can be facilitated by use of a precision stage (e.g., a precision x-y stage) supporting the substrate, wherein positions of the precision stage can be manually and/or automatically adjusted.

In another variation of cell retrieval tool operation, the cannula includes an aperture through the puncture tip. The cannula is advanced through the inlet channel 140, successively blocking each successive pore chamber 113 until only the desired subset of pores 111 are left uncovered. Fluid can then be provided through the outlet channel 150 directly fluidly connected with the uncovered pores 111 to simultaneously release the cells from the uncovered pores 111, wherein the fluid preferably entrains the cells and moves the cells into the cannula. The cannula can additionally or alternatively be fluidly connected to a low-pressure generator to aspirate the cells into the cell collection volume.

Cell removal from the system 100 is preferably automated, but can alternatively be semi-automated or manual. Cell identification can include automatic fixing, permeabilization, staining, imaging, and identification of the cells through image analysis (e.g. through visual processing with a processor, by using a light detector, etc.). Cell removal can include advancement of a cell removal tool 600 to the pore 111 containing the cell of interest 10. Cell removal can additionally include cell removal method selection and/or cell removal tool selection. In another variation, cell identification can semi-automated, and cell retrieval can be automated. For example, cell staining and imaging can be done automatically, wherein identification and selection of the cells of interest can be done manually. In another variation, all steps can be performed manually. However, any combination of automated or manual steps can be used. Furthermore, in other variations, the cell removal tool 600 and/or cell removal operations can include any other suitable tool or operation, such as those described in U.S. Pub. No. 2013/0190212, entitled "Cell Capture System and Method of Use" filed 25 Jul. 2012, which is incorporated herein in its entirety by this reference.

1.5 System—Examples

In an example, as shown in FIG. 1B, the system 100 includes an array 110 including a plurality of 1000 substantially identical pores 111, each connected to an inlet channel 140 at the chamber inlet 114 and an outlet channel 150 at the pore channel 117. In the example, each pore 111 is paired with and substantially co-aligned with an electrophoresis channel 161, such that there are 1000 electrophoresis channels in parallel, fluidly coupled to the outlet channel 150. Each of the electrophoresis channels defines an electrophoresis inlet 163 and an electrophoresis outlet 164, has a substantially constant rectangular cross-section along its length, and is substantially linear (e.g., without any curved portions). Furthermore, each electrophoresis outlet 164 is fluidly coupled to an electrophoresis outlet channel 167 to facilitate distribution of a sieving matrix throughout the system 100. In the example, the outlet channel 150 includes a first port 141 and a second port 142, the outlet channel 150 includes a third port 153 and a fourth port 154, and the electrophoresis outlet channel 167 includes a fifth port 165 and a sixth port 166, wherein each of the ports 141, 142, 153, 154, 165, 166 is in communication with a valve, in order to enable directed transmission of biological samples, fluids, reagents, and matrices throughout the system 100. The array 110, inlet channel 140, outlet channel 150, electrophoresis channels 160, and electrophoresis outlet channel 167 are preferably recesses defined on one broad face of a PMMA substrate 120, formed by hot-embossing a PMMA sheet on an etched silicon mold and are preferably cooperatively defined by a top layer of PMMA laminate that fluidly seals microfluidic structures. The set of electrodes 170 in the example includes gold-coated copper wires that are 0.1 millimeters in diameter, which are laminated between the PMMA substrate 120 and the PMMA laminate proximal the inlet channel 140 and the electrophoresis outlet channel 167, with electrically conductive epoxy that provides electrical contacts for microelectrophoresis. In the example, the inlet channel 140 and the outlet channel 150 each have a depth and width of 100 micrometers, the chambers 113 of the pores 111 each have a depth and width of 30 micrometers, the pore channels 117 each have a depth and a width of 8 micrometers, and the electrophoresis channels 161 each have a depth of 8 micrometers, a width of 30 micrometers, and a length of 15 millimeters.

Figure 9:
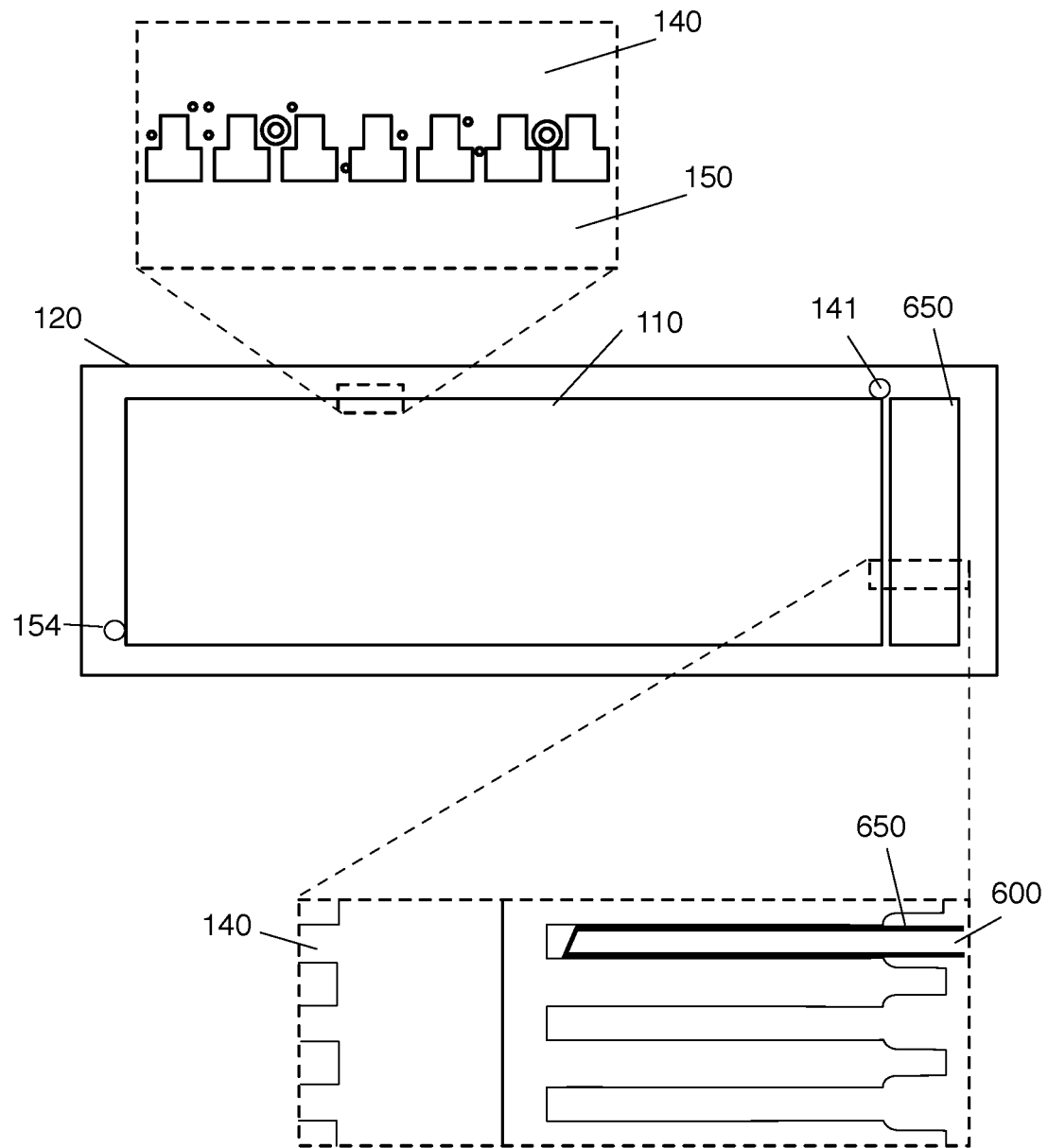
FIG. 9 depicts a specific example of an embodiment of the system.

In another example, as shown in FIG. 9, the system 100 includes a plurality of substantially identical arrays 110 arranged in parallel; an inlet port 141 coupled to an inlet channel 140, and an outlet port 154 coupled to an outlet channel 150. The plurality of arrays includes a plurality of 100,000 substantially identical pores 111 connected to a respective inlet channel 140 at the chamber 113 and a respective outlet channel 150 at the pore channel 117. Each inlet channel 140 is substantially aligned with a guide 650 that facilitates guidance of a cell removal tool 600 into a respective inlet channel 140 for retrieval of a captured cell 10, wherein the guide 650 is separated from a respective inlet channel 140 by a self-sealing barrier configured to form a hermetic seal about the cell removal tool 600 upon penetration. The system 100 in this example allows up to 5 mL of blood to be received at a substantially low pressure (e.g., <10 kPa) in less than 10 minutes. The arrays 110, inlet channels 140, and outlet channels 150 are preferably recesses defined on one broad face of a substrate 120, and are preferably cooperatively defined by a top layer (e.g., PMMA laminate) that fluidly seals the arrays 110, inlet channels 140, and outlet channels 150 from the system 100 exterior. The inlets channels and outlet channels are preferably accessible by holes defined through the thickness of the substrate 120, and preferably originate from the substrate broad face opposing the face defining the arrays 110, inlet channels 140, and outlet channels 150. Additionally or alternatively, the holes can be configured to extend through the substrate 120 from the substrate sides and/or in any other suitable manner.

In other embodiments, variations, and examples, the system 100 can further include any other suitable elements that facilitate cell processing and analysis. Additionally, as a person skilled in the field of cell sorting will recognize from the previous detailed description and from the figures and claims, modifications and changes can be made to the embodiments, variations, examples, and specific applications of the system 100 described above without departing from the scope of the system 100.

2. Method

Figure 10A:
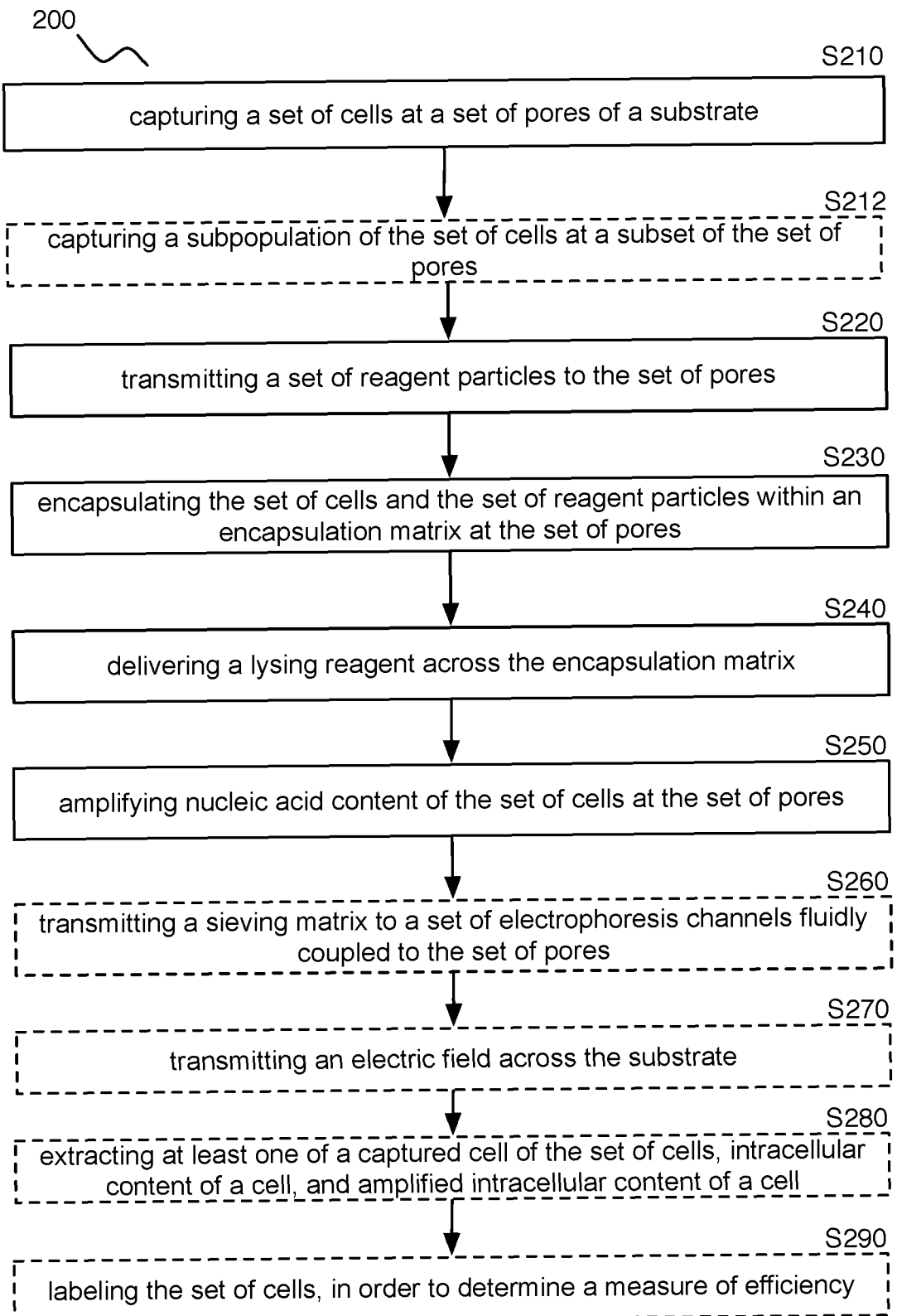
FIGS. 10A and 10B are schematic representations of an embodiment of a method for capturing and analyzing cells.
Figure 10B:
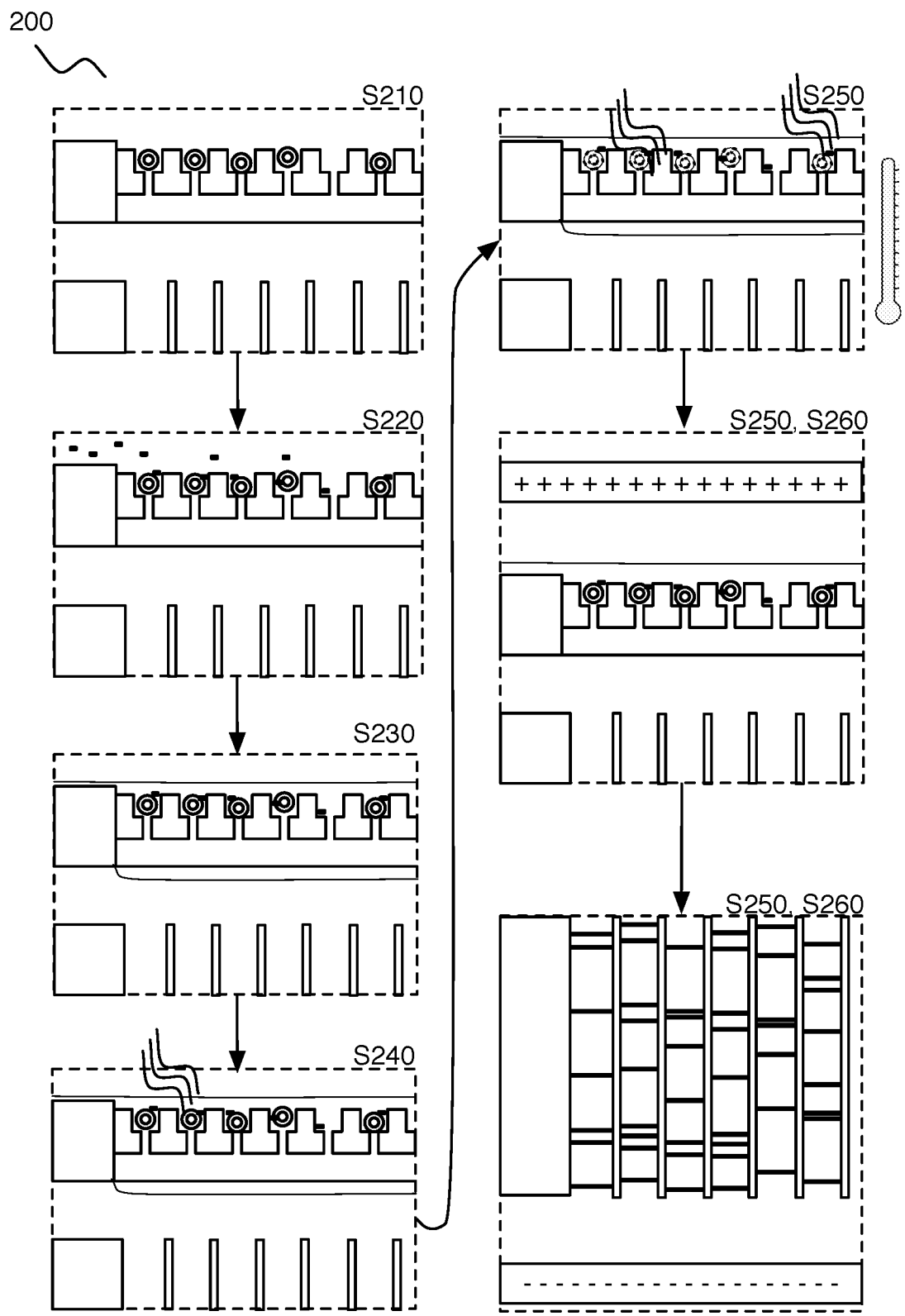
Figure 11:
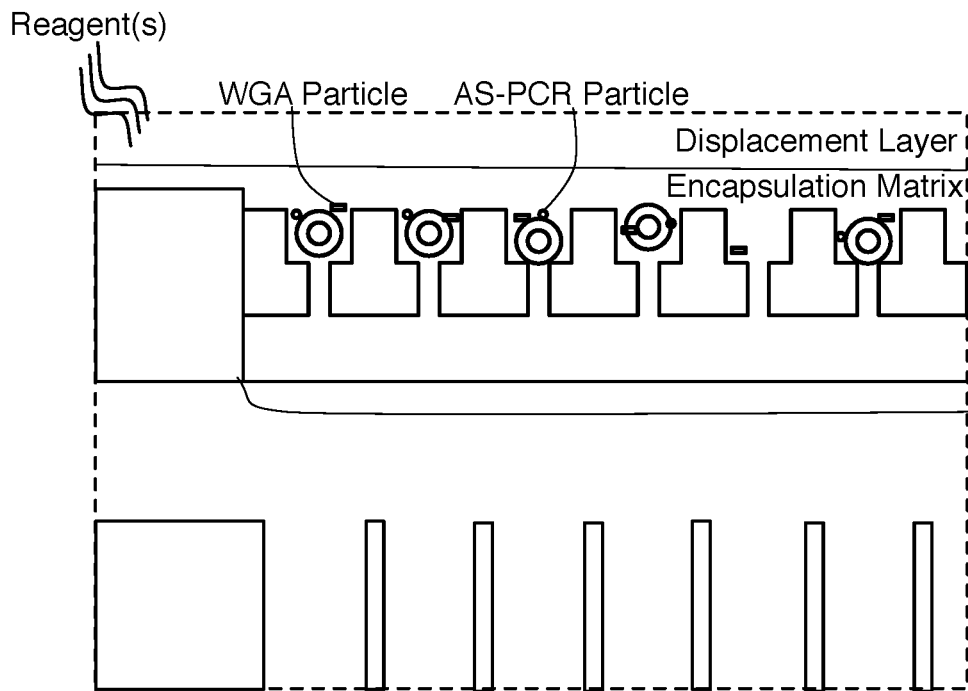
FIG. 11 depicts a portion of an embodiment of a method for capturing and analyzing cells.

As shown in FIGS. 10A and 10B, a method 200 for capturing and analyzing a set of cells comprises: capturing the set of cells S210 at a set of pores of a substrate, each pore including a chamber configured to hold a single cell of the set of cells; transmitting a set of reagent particles to the set of pores S220, wherein the set of reagent particles is configured to facilitate whole genome amplification and polymerase chain reaction (PCR) of each cell in the set of cells; encapsulating the set of cells and the set of reagent particles within an encapsulation matrix at the set of pores S230; delivering a lysing reagent across the encapsulation matrix, thereby lysing the set of cells S240; and amplifying nucleic acid content of the set of cells at the set of pores, thereby facilitating analysis of the set of cells S250. In some variations, the method 200 can further include transmitting a sieving matrix to a set of electrophoresis channels fluidly coupled to the set of pores S260; and transmitting an electric field across the substrate S270, thereby enabling electrophoretic analysis of the set of cells.

The method 200 functions to enable isolation, capture, and retention of cells, more preferably single cells, at known, addressable locations, and further to facilitate performance of multiple single-cell assays that can be performed on individual cells (e.g., rare cells in a biological sample). The method 200 is preferably implemented at least in part using the system 100 described in Section 1 above; however the method 200 can additionally or alternatively be implemented using any other suitable system 100 for cell capture and analysis. In some embodiments, the method 200 can be used to capture circulating tumor cells (CTCs) and subpopulations of CTCs, such as circulating stem cells (CSCs), but can additionally or alternatively be used to capture any other suitable cell of possible interest for processing and analysis.

Block S210 recites: capturing the set of cells at a set of pores of a substrate, each pore including a chamber configured to hold a single cell of the set of cells, which functions to segregate cells of interest within chambers configured to retain a single cell, in order to facilitate analyses of the set of cells in a single-cell format. Block S210 is preferably implemented at a set of pores of an embodiment of the array of the system 200 described in Section 1.1 above. The set of cells are preferably carried in a volume of a biological sample, and in some variations, can include a volume of blood or any other suitable digested tissue. The set of cells are thus cells of interest (e.g., circulating tumor cells, stem cells, etc.) that are carried in the biological sample, but in some variations, can include cells or other particles that are spiked into the biological sample (e.g., for research applications).

In a specific example, Block S210 includes receiving a biological sample (e.g., a volume of blood collected by venipuncture from donors and stored in EDTA-treated containers, a volume of saline/bovine serum albumin/EDTA buffer), wherein the biological sample is spiked with a number (e.g., 1, 5, 50, 100, 200, etc.) breast cancer cell line MCF 7 cells. In the specific example, the MCF 7 cells are maintained in Eagle's Minimum Essential Media (EMEM) supplemented with 10% fetal bovine serum (FBS) and 100 units per milliliter of Penicillin-Streptomycin, and grown at 37 C in a humidified incubator (e.g., 95% humidity) in a 5% carbon dioxide environment prior to harvesting and spiking into the biological sample. The biological sample with the cells of interest is then mixed with fixative (e.g., an equal volume of 1% paraformaldehyde, equal volume of 2% formalin) and received (e.g., by way of a pump providing less than 1 psi of pumping pressure) at a first port of an inlet channel coupled to the set of pores, and transmitted through the set of pores to capture the set of cells. Undesired biological sample components are passed through a set of pore channels coupled to the pores, to an outlet channel coupled to a fourth port for waste removal. In the specific example, a pore chamber depth of 8 micrometers and a pumping pressure less than 1 psi allows the cancer cells of interest (i.e., MCF 7 cells that are 15-30 micrometers in diameter) to be retained at the set of pores, while red blood cells and white blood cells pass through and are not captured. In variations of the specific example, a priming buffer can be received into the inlet channel and the set of pores prior to reception of the biological sample, wherein the priming buffer prevents trapping of air bubbles, which can obstruct sample processing. However, in other variations, Block S210 can be implemented using any other suitable system configured to capture and isolate cells of interest in a single cell format.

Block S210 preferably includes capturing the set of cells without the use of affinity molecules configured to bind to a cell of the set of cells, such that captured cells undergo minimal manipulation and can be retrieved for further processing; however, capturing the set of cells in Block S210 can alternatively include implementation of any suitable affinity mechanism, and in some variations, can include any one or more of: electric field traps, microfluidic features that direct sample fluid flow into a pore, negative pressure application to the outlet channel 150, affinity molecules, chemotaxic gradients that attract cells in a desired direction, magnetic tagging and manipulation of tagged particles by a magnetic field, and any other suitable affinity mechanism. In Block S210, the set of cells preferably includes CTCs, such that Block S210 includes capturing substantially all (e.g., over 85%) CTCs present in a biological sample at the set of pores. However, Block S210 can additionally include capture of heterogeneous populations of cells, with any suitable efficiency, at a set of pores. Furthermore, some variations of Block S210 can include capture of multiple cells in a single pore, such that capture is not single-format.

In some variations, as shown in FIG. 10A, Block S210 can further include capturing a subpopulation of the set of cells at a subset of the set of pores S212, such that populations and subpopulations of a cell-type of interest can be captured in a single-cell format for analysis. In such variation, Block S210 can include capturing a set of CTCs at the set of pores in single-cell format, and Block S212 can include capturing a subpopulation of self-renewing cancer stem cells (CSCs), which are associated with treatment resistance and higher metastatic potential. In Block S212, the subpopulation of the set of cells is preferably captured simultaneously with the set of cells using a set of identical pores based upon size and deformability properties, with identification and single-cell analyses performed in subsequent steps. However, Block S212 can be performed non-simultaneously with Block 210, can be performed using non-identical pores (e.g., a set of pores including pores configured to capture CTCs and pores configured to capture CSCs), and/or can be performed in any other suitable manner.

Block S220 recites: transmitting a set of reagent particles to the set of pores, which functions to deliver activateable reagents to the captured cells of interest, prior to encapsulation in Block S230 and/or analysis to discriminate between captured cells of interest and contaminants. In variations, the reagent particles can include microspheres (magnetic or non-magnetic) containing affinity molecules to bind nucleic acids (e.g., total nucleic acid, DNA, RNA) or nucleic acid containing specific oligonucleotide sequences, antibodies, or polypeptides. In one example, and similar to reception of the set of cells, the set of reagent particles are received at a first port of an inlet channel coupled to the set of pores, and captured at pores of the set of pores containing a captured cell of the set of cells. In the example, excess reagent particles are passed through a set of pore channels coupled to the pores, to an outlet channel coupled to a fourth port for waste removal. The set of reagent particles are preferably sized such that the reagent particles are caught between a cell captured in a pore, and a wall of the pore, but are unable to escape because of the presence of the cell abutting a pore channel coupled to the pore; however, the reagent particles can be characterized by any other suitable property (e.g., adhesive behavior, viscosity, morphology, etc.) that enables delivery and capture of the set of reagent particles at pores containing a captured cell of interest. In one alternative variation, however, a pore can be configured to uniformly capture reagent particles and cells of interest in any suitable order, for instance, due to geometric configurations of the pore (e.g., the pore comprises a first compartment that is complementary to a reagent particle and a second compartment that is complementary to a cell of interest, wherein the first compartment and the second compartment are in fluid communication).

In some variations, as shown in FIGURE ii, the set of reagent particles is configured to facilitate whole genome amplification (WGA) and allele specific polymerase chain reaction (AS-PCR) or target specific PCR of each cell in the set of cells, however, the set of reagent particles can alternatively be configured to facilitate only one of WGA and AS-PCR. Additionally or alternatively, the set of reagent particles can be configured to facilitate any other type of genetic amplification (e.g., for any other type of PCR, for multiple annealing and looping based amplification cycles, for loop-mediated amplification, for transcription-mediated amplification, for nucleic acid sequence based amplification, etc.) in order to amplify content. In variations wherein reagent particles for multiple types of amplification (or other processing) are co-received and transmitted, the set of reagent particles can include particles of different properties (e.g., melting temperatures, etc.) in order to facilitate sequential processing of the set of cells according to the different types of amplification (or other processing). In a specific example, the reagent particles for WGA include particles 6 micrometers in diameter composed of low-melting agarose (e.g., melting point of 65 C) coated with random hexamer primers required for WGA. In a specific example, the reagent particles for AS-PCR include particles 6 micrometers in diameter composed of polystyrene and processed with conjugated forward primers for AS-PCR.

In some variations, Block S220 can additionally or alternatively include receiving reagents at the set of pores, wherein the reagents are configured to facilitate identification of a subpopulation of the set of cells captured at a subset of the set of pores (e.g., captured, as in Block S212). Block S220 can thus include transmitting a reagent volume to the set of pores and/or can include receiving and transmitting reagents in any other suitable manner. In one variation, the regents can include an antibody cocktail configured to facilitate distinguishing of a subpopulation of cells (e.g., CSCs) from the set of cells (e.g. CTCs), wherein incubation with antibody cocktail can enable identification of the subpopulation of cells by fluorescent detection. In examples of this variation implemented at an embodiment of the system 100 described above, the reagents can be received into the inlet channel (e.g., at the first port) coupled to the set of pores, and delivered to captured cells at the set of pores. In a specific example of this variation, the antibody cocktail can include CD24 and CD44 antibodies, wherein expression of a CD44+/CD24− phenotype facilitates identification of CSCs from a set of CTCs. The antibody cocktail in the specific example can further include CAM 5.1 (CK8/18) antibodies, which can help distinguish cancer cells (e.g., CTCs, CSCs) of the set of cells from contaminating cells (e.g., leukocytes). In the specific example, the antibody cocktail is delivered into the first port of an inlet channel fluidly coupled to the set of pores containing captured cells, with Hoechst nuclear stain as a counter stain. The antibody cocktail is then incubated with the set of cells and the subpopulation of cells, after which fluorescent detection is used to facilitate retrieval and/or downstream analyses of the subpopulation of CSCs. In variations of the specific example, antigen retrieval and/or alternative fixation processes can facilitate processing and detection of CSCs of the set of CTCs. In one such variation, alternative fixatives (e.g., alternatives to formalin) can include −20 C methanol, acetone, and 1:1 methanol-acetone, and antigen retrieval can be conducted using one or more of: citrate buffer, SDS (detergent), and enzymatic treatment (e.g., trypsin, proteinase K). Additionally or alternatively, variations of the specific example can include combination of fluorescent markers with bright field staining (e.g., with methylene blue, with eosin, with DAPI) in order to mitigate interference (e.g., spectral overlapping of fluorophores) produced during "multi-color" staining. As such, distinguishing the subpopulation of cells can include transmitting excitation wavelengths of light to captured cells in the set of pores, and/or receiving emitted light from fluorophores bound to the set of cells. However, in other variations, the reagents can include any other suitable reagents that distinguish at least one subpopulation of cells from the set of cells (e.g., by enabling detection of any other suitable biomarker phenotype), the reagents can be delivered in any other suitable manner, using any other suitable system, and any other suitable fixation, antigen retrieval, and/or staining protocol can be used.

Block S230 recites: encapsulating the set of cells and the set of reagent particles within an encapsulation matrix at the set of pores, and functions to isolate captured cells of interest and reagents in a single-cell format, in order to facilitate further processing and analysis of the set of cells at a single-cell level. The encapsulation matrix preferably isolates a pore and its contents within an array, in an embodiment of the system 100 described above; however, the encapsulation can isolate cells and reagent particles in any other manner and/or in any other suitable system. The encapsulation matrix preferably has a flow state and a set state, wherein a photochemical reaction, thermochemical reaction, polymerization reaction and/or any other suitable reaction switches the encapsulation matrix from the flow state to the set state. In the flow state, the encapsulation matrix is preferably substantially viscous, such that the encapsulation matrix does not flow into the pores during introduction into the system 100. In the set state, the encapsulation matrix is preferably a solid or gel that prevents particle egress from the pores 111 (e.g., egress of cells, reagent particles, and large nucleic acid molecules from the pores), and is preferably porous or selectively permeable to permit small molecule, buffer, and reagent (e.g., detergent, enzyme, primer, etc.) penetration therethrough. Furthermore, by changing the constituents of a buffer or reagent and allowing sufficient time for diffusion, specific reagents/buffers can be entered into or eluted out from encapsulated cells. In one variation, the encapsulation matrix is a microporous agarose gel with a low melting point, and in another variation, the encapsulation matrix is a photopolymerizable hydrogel, such as PEG or polyacrylamide with photoinitiator; however, the encapsulation matrix can alternatively be any suitable material with any other suitable polymerization agent.

In a specific example of Block S230, implemented at an embodiment of the array, the inlet channel, and the outlet channel of the system 200 described above, the encapsulation matrix is a low melting agarose gel that is received in its flow state at the first port of the inlet channel, and transmitted across the set of pores containing captured cells and reagent particles, wherein excess encapsulation matrix is transmitted to the fourth port of the outlet channel to facilitate even distribution of the encapsulation matrix. A portion of the encapsulation matrix upstream of the pore channels is then replaced by a displacement fluid (e.g., air, immiscible fluid, oil) by transmission of the displacement fluid from the first port of the inlet channel to the second port of the inlet channel, thereby forming a displacement layer. The displacement layer facilitates diffusion of reagents and buffers across the encapsulation matrix for further processing of the set of cells. In the example, upon cooling of the agarose gel below its gel point, the cells and reagent particles are entrapped at the set of pores by the setting of the encapsulation matrix.

Block S240 recites: delivering a lysing reagent across the encapsulation matrix, thereby lysing the set of cells, and functions to release intracellular content of the set of cells, which can be amplified and processed in order to individually analyze each cell of the set of cells. The lysing reagent can additionally or alternatively include protein-digesting reagents (e.g., pepsin, proteinase K). In Block S240, lysing preferably includes delivering the lysing reagent to an interface of the encapsulation matrix (e.g., at a displacement layer generated by delivering a displacement fluid through the inlet channel), such that the lysing agent can diffuse across the encapsulation matrix to a cells captured at the set of pores. The lysing reagent can be delivered at low pressure to facilitate passive diffusion, or can be provided with pressure (e.g., positive pressure, negative pressure), in order to drive the lysing reagent across the encapsulation matrix. In one variation, the lysing reagent comprises detergent and alkaline buffer that can traverse across the porous encapsulation matrix. In a specific example, the lysing reagent comprises 5 microliters of 0.4 M KOH with 10 mM EDTA and 50 mM DTT, which is incubated with the set of cells at 65 C for 10 minutes. In the specific example, lysis is subsequently terminated by adding 5 microliters of a neutralizing buffer including 0.9 M Tris-HCl buffer at pH 8.3, with 0.3 M KCl and 0.2 M HCl. However, in other variations of Block S240, the lysing reagent can include any other suitable lysing reagent, and/or lysis can be terminated in any other suitable manner. In Block S240, lysing can further comprise heating the set of cells, the set of reagent particles, and the lysing reagent in order to facilitate cell lysis. In variations, heating can be performed at a constant temperature or with a variable temperature profile. In a specific example, implemented at an embodiment of the system 100 described above, the lysing reagent can be received at the first port and transmitted to the second port of the inlet channel, and a region of the substrate proximal the set of pores can be heated with a thermocycler (e.g., a block thermocycler comprising one or more heating elements), in order to further enhance lysis. In Block S240, reagent products can further be removed post-lysis, by equilibrating contents of cell sacs produced by lysis with a suitable buffer.

Block S250 recites: amplifying nucleic acid content of the set of cells at the set of pores, thereby facilitating analysis of the set of cells, which functions to amplify genetic content in order to facilitate downstream analyses of the set of cells at a single-cell level. In one variation, amplifying nucleic acid content of the set of cells can facilitate downstream analyses of the set of cells using electrophoretic assays; however, in other variations, amplifying nucleic acid content of the set of cells can facilitate any other suitable assay. In some variations, downstream assays utilizing amplified nucleic acid content of the set of cells can be implemented "on-chip" using an embodiment of the system 100 described above; however, in other variations, amplified nucleic acid content can be retrieved from a system and analyzed off-chip using any other suitable method.

Figure 12:
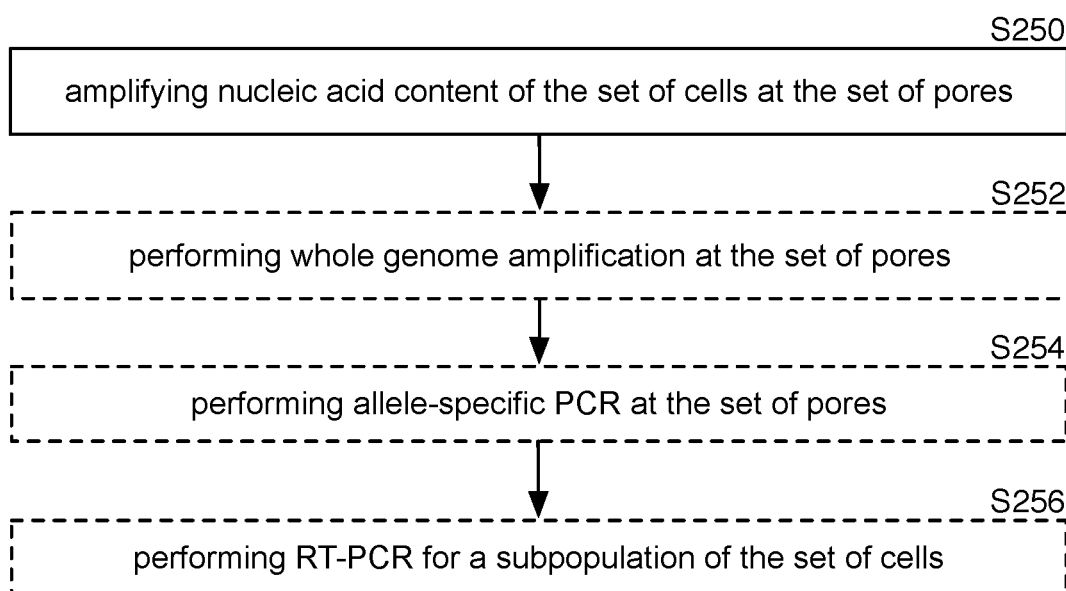
FIG. 12 depicts a portion of an embodiment of a method for capturing and analyzing cells.

In some variations, as shown in FIG. 12, Block S250 can include performing whole genome amplification (WGA) at the set of pores containing lysed cells S252, which functions to expand a quantity of nucleic acid content of a cell of the set of cells, in order to facilitate downstream analyses of the set of cells requiring a sufficient quantity of genetic content. In some variations, Block S252 can function to provide a sufficient quantity of nucleic acids (e.g., DNA, RNA) for further multiplex AS-PCR (e.g., as in Block S254) for mutation analysis. In one variation, Block S252 can include performing WGA by multiple displacement amplification (MDA), which is a non-PCR based DNA amplification technique wherein amplification can take place at a constant temperature (e.g., 30 C). As such, in variations of Block S252 implementing at least a portion of the system 100 described above, a region of the substrate proximal the set of pores can be isothermally incubated (e.g., isothermally incubated in a thermocycler) in order to drive the WGA process to completion; however, in other variations, the lysed cells can be incubated in any other suitable manner. In a specific example, bacteriophage φ29 DNA polymerase and random exonuclease-resistant hexamer primers are used in an isothermal reaction at the set of pores for MDA. In the specific example, the bacteriophage φ29 DNA polymerase has high processivity, generating amplified fragments of <10 kb by strand displacement, and has proof-reading activity resulting in low misincorporation rates. In the specific example, a master mix is prepared using REPL-g reaction buffer and REPL-g DNA polymerase with nuclease-free water, which is flowed into the inlet channel of an embodiment of the system 100 described above at the first port. The substrate is then incubated at 30 C for 8-18 hours followed by heating of the substrate for 3 minutes at 65 C to inactivate the REPL-g DNA polymerase. In variations of the specific example, the yield of amplified genetic content (e.g., DNA) can subsequently be measured using a fluorochrome specific for double stranded DNA (e.g., SYBR green). In other variations of Block S252, however, WGA can be performed in any other suitable manner, such as a PCR-based technique for WGA (e.g., degenerate oligonucleotide PCR, primer extension preamplification).

In some variations, as shown in FIG. 12, Block S250 can additionally or alternatively include performing AS-PCR at the set of pores containing lysed cells S254, which functions to enable detection of at least one mutation or other identifying feature characterizing cells of the set of cells. In some variations, Block S254 can enable development of multiplex biomarker panels for detection of a type of breast cancer (e.g., biomarker panels for breast cancer); however, Block S254 can additionally or alternatively enable development of any other suitable marker profile for any other suitable cell-type of interest. Preferably, performing AS-PCR in Block S254 is based upon discrimination by Taq polymerase between a match and a mismatch at the 3' end of a PCR primer. In a specific example, Block S254 includes performing AS-PCR at an embodiment of the system 100 described above, wherein 25 microliters of a PCR master mix including HotStartTaq, Type-it mutation detection buffer, dNTPs, and an equal concentration of primer (e.g., to a final concentration of 0.25 µM) is delivered into the first port of the inlet channel and allowed to diffuse across the encapsulation matrix to the lysed set of cells (e.g., the cell sacs) at the set of pores. PCR amplification in the specific example is then carried out using the following thermocycling parameters: 95 C for five minutes for initial activation, followed by 35 cycles of 95 C for 30 seconds, 60 C for 90 seconds, and 72 C for 30 seconds, followed by a final extension of 68 C for 10 minutes. In the example, conjugation of the forward primers on one end to the reagent particles delivered in Block S220 allows localization of amplified amplicons at the set of pores.

In the specific example of Block S254 described above, and variations thereof, primer pairs for AS-PCR to detect single nucleotide polymorphism (SNP) mutations for cell biomarkers (e.g., breast cancer biomarkers) can be used, as shown in FIG. 13. In the specific example, for each SNP mutation, two AS forward primers and a reverse common primer are preferably required. Furthermore, a tail is incorporated in the AS primers, thus allowing differentiation of the alleles through the length of the PCR amplicon on the encapsulation matrix (e.g., agarose gel). In one example of design of forward primers for AS-PCR, a forward primer can be designed without a tail, and a 5-base pair short tail can be added to the 5' end of a wild type forward primer, while a 15-base pair long tail can be added to the 5' end of a mutant forward primer, which allows discrimination of 10-base pairs to be detected between two AS-PCR amplicons. In the example, the melting temperature can be configured to be between 50 C and 65 C, with no more than 5 C difference between melting temperatures for the wild type forward primer, the mutant forward primer, and a common reverse primer. Furthermore, in the specific example, to multiplex AS-PCR for detecting multiple mutations (e.g., 5 mutations) simultaneously, multiple mutations (e.g., five breast cancer mutations) with different amplicon sizes differing by at least 20 base pairs can be chosen. However, in other variations and examples, any other suitable forward primers with any other suitable number of tail base pairs for wild type and/or mutant primers can be chosen, any other suitable reverse primers can be chosen, primers can be chosen with any other suitable melting temperature, the multiplex AS-PCR can be configured to detect any other suitable number of mutations, and the mutations can be characterized by any other suitable amplicon size (e.g., number of base pairs). Furthermore, In other variations of Block S254, performing AS-PCR can alternatively be based upon discrimination using any other suitable master mix incorporating any other suitable polymerase(s), discrimination between a match and a mismatch at any other suitable location of a genetic sequence, and/or any other suitable thermocycling profile.

In variations wherein reagent beads for WGA and AS-PCR are co-delivered in Block S220, to prevent interference from effects of forward primers for AS-PCR on the WGA process, the forward primers for AS-PCR in Block S254 can be modified with one or more thermolabile 4-oxo-1-pentyl (OXP) phosphotriester (PTE) modification groups at 3'-terminal and 3' penultimate inter nucleotide linkages. The OXP PTE modifications can thus impair polymerase primer extension at the lower temperatures that exist prior to PCR amplification in Block S254. Interference from the forward primers can, however, be mitigated using any other suitable modification groups, and/or in another suitable manner.

In some variations, as shown in FIG. 12, Block S250 can additionally or alternatively include performing RT-PCR for a subpopulation of the set of cells S256, in order to facilitate comparisons of gene expression for a subpopulation of the set of cells. Block S256 can be performed at the set of pores before or after encapsulation in Block S230, or can additionally or alternatively be performed after cell retrieval (e.g., in variations of the method 200 incorporating Block S280). In one variation, Block S256 can include performing qRT-PCR on a subpopulation of captured CSCs in order to compare their gene expression with other cancer cells and leukocytes (e.g., from a biological sample comprising a volume of blood). In a specific example of this variation, the subpopulation of CSCs can be incubated (e.g., on-chip, off-chip) with a reverse transcription and pre-amplification master mix (e.g., CellDirect One-step qRT-PCR kit), with SUPERase® RNAse inhibitor. Post-amplification in the specific example, threshold cycle values for a group of target genes (e.g., Her2, ALDH1, TWIST1) and an internal control (e.g., 18S rRNA) can be determined and recorded and relative quantitation of gene expression can be calculated using comparative CT ($\Delta\Delta CT$) and/or any other suitable method. However, Block S256 can alternatively include performing any other suitable type of PCR for any other suitable subpopulation of the set of cells.

As shown in FIG. 10A, the method 200 can further include Block S260, which recites: transmitting a sieving matrix to a set of electrophoresis channels fluidly coupled to the set of pores. Block S260 functions to provide a porous matrix that is continuous between the set of pores and throughout the set of electrophoresis channels, in order to form a continuous path for electrophoretic separation of amplified intracellular content. The sieving matrix is preferably similar to or identical in composition to the encapsulation matrix delivered in Block S230, and in a specific example, comprises 3% agarose. However, the sieving matrix can alternatively include any other suitable material that facilitates electrophoretic separation in Block S270. Additionally, the sieving matrix preferably matrix preferably has a flow state and a set state, wherein a photochemical reaction, thermochemical reaction, polymerization reaction or any other suitable reaction switches the sieving matrix from the flow state to the set state. In the flow state, the sieving matrix can thus be delivered to the set of electrophoresis chambers and evenly distributed across them, and in the set state, the sieving matrix is preferably a solid or gel that is preferably porous or selectively permeable to permit small molecule, buffer, and reagent penetration therethrough. In a specific example of Block S260 implementing an embodiment of the system 100 described above, the sieving matrix is received under pressure at the third port of the outlet channel and excess sieving matrix is passed out of the sixth port of the electrophoresis outlet channel. Subsequent to sieving matrix delivery, separation buffer (e.g., 1× TBE buffer with 0.5 µg/mL ethidium bromide) is then received at the first port, the second port, the third port, the fourth port, the fifth port, and the sixth port of the substrate and diffused across the encapsulation matrix/sieving matrix. The separation buffer can include fluorescence dye that can facilitate identification of the size and location of a separated amplicon, and/or any other suitable component that facilitates identification of specific amplicons (e.g., in bands produced by electrophoresis). However, in other variations, the sieving matrix can be delivered in any other suitable manner (e.g., by positive pressure, by negative pressure), transitioned to a set state in any other suitable manner, and/or delivered with a separation buffer comprising any other suitable factors.

Also shown in FIG. 10A, the method 200 can further include Block S270, which recites: transmitting an electric field across the substrate, thereby enabling electrophoretic analysis of the set of cells. Block S270 functions to provide a driving force that electrokinetically separates amplified intracellular content from the set of cells, based upon size and charge of the content. In some variations, Block S270 can include heating the substrate, which can facilitate release of amplified products from reagent particles (e.g., primer beads); however, variations of Block S270 can entirely omit heating the substrate, and/or can include facilitating release of amplified products in any other suitable manner (e.g., by pH shift). Preferably, transmitting the electric field across the substrate includes applying a substantially large electric field (e.g., a few kV/centimeter) across electrodes coupled to the substrate, using a voltage regulator. In variations implemented at an embodiment of the system 100 described above, the electric field is preferably provided at the set of electrodes coupled at the substrate proximal the inlet channel and the electrophoresis outlet channel; however, the electric field can alternatively be provided in any other suitable manner at any other suitable apparatus configured to generate an electric field that provides a suitable force for electrokinetic separation. Bands produced by electrophoretic separation can subsequently be viewed under fluorescence microscopy for detection of the intensity and relative location of bands, and/or in any other suitable manner for electrophoretic analysis of the set of cells. As such, the method 200 can enable distinguishing of amplicons based upon size and color (i.e., by fluorophores), in order to facilitate examination of multiple biomarkers in at least two different manners.

In some variations, as shown in FIG. 10A, the method 200 can additionally or alternatively include Block S280, which recites: extracting at least one of a captured cell of the set of cells, intracellular content of a cell of the set of cells, and amplified intracellular content of a cell of the set of cells. Block S280 functions to extract a cell of interest and/or intracellular content of a cell of interest from the substrate, in order to facilitate further analyses of a cell of the set of cells in a single-cell format. In variations of Block S280 including extracting a captured cell of the set of cells, the captured cell is preferably extracted individually from a pore of the set of pores; however, in some variations multiple cells of the set of cells can be extracted at the set of pores simultaneously. In one variation, implementing an embodiment of the system 100 described above, a cell removal tool can be used to extract at least one captured cell (e.g., a CSC, a contaminating leukocyte, a CTC, etc.), wherein the cell removal tool is configured to penetrate the inlet channel (e.g., at one or more of the first port and the second port), and facilitate extraction of a captured cell directly from a pore. In one example, the cell can be aspirated into the cell removal tool, and in another example, the cell can be pushed into the cell removal tool (e.g., by providing a positive pressure at the outlet channel). In still other variations, however, the captured cell can be extracted in any other suitable manner.

In variations of Block S280 including extracting intracellular content of a cell of the set of cells, the intracellular content/cell sacs of lysed cells of the set of cells can be extracted by accessing the pore(s) of the set of pores containing the lysed cellular content, prior to amplification of intracellular content. In one variation, the intracellular content can be extracted by harvesting encapsulation matrix of at least one pore. In a specific example implemented at an embodiment of the system 100 described above, the encapsulation matrix of a pore can be excised (e.g., by incision of a PMMA/COP laminate) to extract the intracellular content. However, in other variations, the intracellular content can be extracted in any other suitable manner for any other suitable downstream application. In variations of Block S280 including extracting amplified intracellular content of a cell of the set of cells, amplified intracellular content can be extracted by harvesting encapsulation matrix containing the amplicons generated in variations of Block S250. In specific examples of these variations, implemented at an embodiment of the system 100 described above, the encapsulation matrix with amplicons can be excised (e.g., by incision of a PMMA/COP laminate) from each pore of the set of pores, in order to facilitate downstream assays performed "off-chip" (e.g., off-chip electrophoresis). However, the amplified intracellular content can be extracted in any other suitable manner, and/or for any other suitable downstream application.

In some variations, the method 200 can additionally or alternatively include Block S290, which recites labeling the set of cells, in order to determine a measure of efficiency. Block S290 functions to enable measurement of an efficiency of cell capture by a system 100 for capturing and analyzing cells in a single-cell format, which can be used to improve efficiency in the system and/or to identify causes of inefficiencies in the system. Block S290 can be implemented prior to reception of the set of cells in Block S210, simultaneously with reception of the set of cells in Block S210, and/or in any other suitable manner. Post capture at the set of pores, the labeled cells can be imaged using fluorescence microscopy and/or any other suitable optical detection module (or other module) in order to discriminate captured cells of interest from captured contaminants. In one variation, labeling can include labeling the cells with Cell Tracker green dye, which, in a specific example, includes centrifuging the set of cells at 1000 rpm for 5 minutes, removing a supernatant, and adding 6 milliliters of serum-free media and 5 microliters of Cell Tracker dye to the centrifuged cells, with incubation at 37 C for 30 minutes. In the specific example, the dyed cells can then be centrifuged at 1000 for 5 minutes with subsequent supernatant removal, washed in saline (e.g., 1× PBS), and resuspended in 10 milliliters of complete growth medium. In another variation, labeling in Block S290 can include antibody staining of the set of cells. In a specific example, antibody staining can be implemented "on-chip" using an embodiment of the system 100 described above, wherein prior to receiving a biological sample, surfaces of fluidic channels of the substrate are coated by running 8 mL of 1× PBS/1% BSA/2 mM EDTA buffer for 10 minutes in order to prevent cell adhesion and bubble trapping. In the specific example, buffer (e.g., 1.5 mL of PBS/BSA/EDTA) can be added to dilute a fixative solution mixed with the biological sample, and the biological sample can be received by way of a pump configured to provide 6 kPA of pressure. In the specific example, the captured cells are washed with 3 mL of wash buffer (e.g., PBS/BSA/EDTA) and incubated with 2 mL of 4% formalin/1% BSA/0.1% Triton for 10 minutes, which is followed by another wash with 2 mL of wash buffer. The captured cells are then incubated with 4 mL of 5% goat serum for 20 minutes, after which the goat serum is replaced with 1 mL of primary antibody cocktail comprising 1:200 CAM5.2, 1:400 CD45, and 1:1000 Hoechst stain and incubated for 45 minutes. In the specific example, the stained captured cells are then washed with 2 mL of wash buffer, incubated with 2 mL of secondary antibody cocktail (e.g., 3 micrograms/mL of Alexa 488, 3 micrograms/mL of Alexa 568) for 30 minutes, and then washed again with 2 mL of wash buffer. The stained captured cells are then observed under fluorescence microscopy in order to discriminate cells of interest from contaminants. However, labeling in Block S290 can include any other suitable type of labeling that allows for discrimination between captured cells of interest and contaminants.

2.1. Method—Example Application Areas

The method 200 described above can be used for a variety of biological assays and procedures. Running an assay or procedure preferably includes capturing and isolating target cells in addressable locations within the system and delivering reagents to the interior or surface of each captured cell while maintaining cell registration with its respective pore or location. Post-delivery of reagents, the captured target cells and/or intracellular content produced by cell-lysis can either be processed and analyzed on-chip, or can be harvested for processing and analysis off-chip. Cell analysis is preferably used to determine the morphology of the captured cells, to examine additional phenotypic expressions of the captured cells (e.g., by biomarker characterization), and to determine the number and location of captured cells of interest. Cell analysis is preferably performed by an associated integrated platform 30, wherein morphology, biomarker expression (e.g., as examined under fluorescence), and cell counting are preferably accomplished through global chip imaging and image analysis. Imaging and analysis is preferably automatically performed, but can alternatively be semi-automated or manually performed. However, morphology determination, biomarker expression, and cell counting can be achieved through any other suitable method.

Running assays on the isolated cells functions to determine characteristics of the cells and/or determine cell responses to given stimuli. Analyses can be run on the cells individually (e.g. single cell level analysis), wherein cells can be individually fluidly isolated within the system 100. Alternatively, analyses can be run on the system 100 as a whole. Example assays that can be run on the cells include FISH assays, mRNA FISH assays, ISH assays, selective cell lysing and lysate collection, single cell molecular analysis (e.g. PCR, RT-PCR, Whole Genome Amplification, ELISPOT, ELISA, Immuno-PCR, etc.), drug testing, cell culturing, affinity analyses, time-responsive analyses, but other analyses can alternatively/additionally be run. Isolated cells can be removed prior to, during, or after the assays have been run, preferably with the cell removal tool 600 but alternatively with any suitable method. Alternatively, isolated cells can be isolated within the chamber 113 (e.g. with an isolation layer), fixed, cultured within the chamber 113, or be retained within the chamber 113 in any other suitable manner.

Figure 14A:
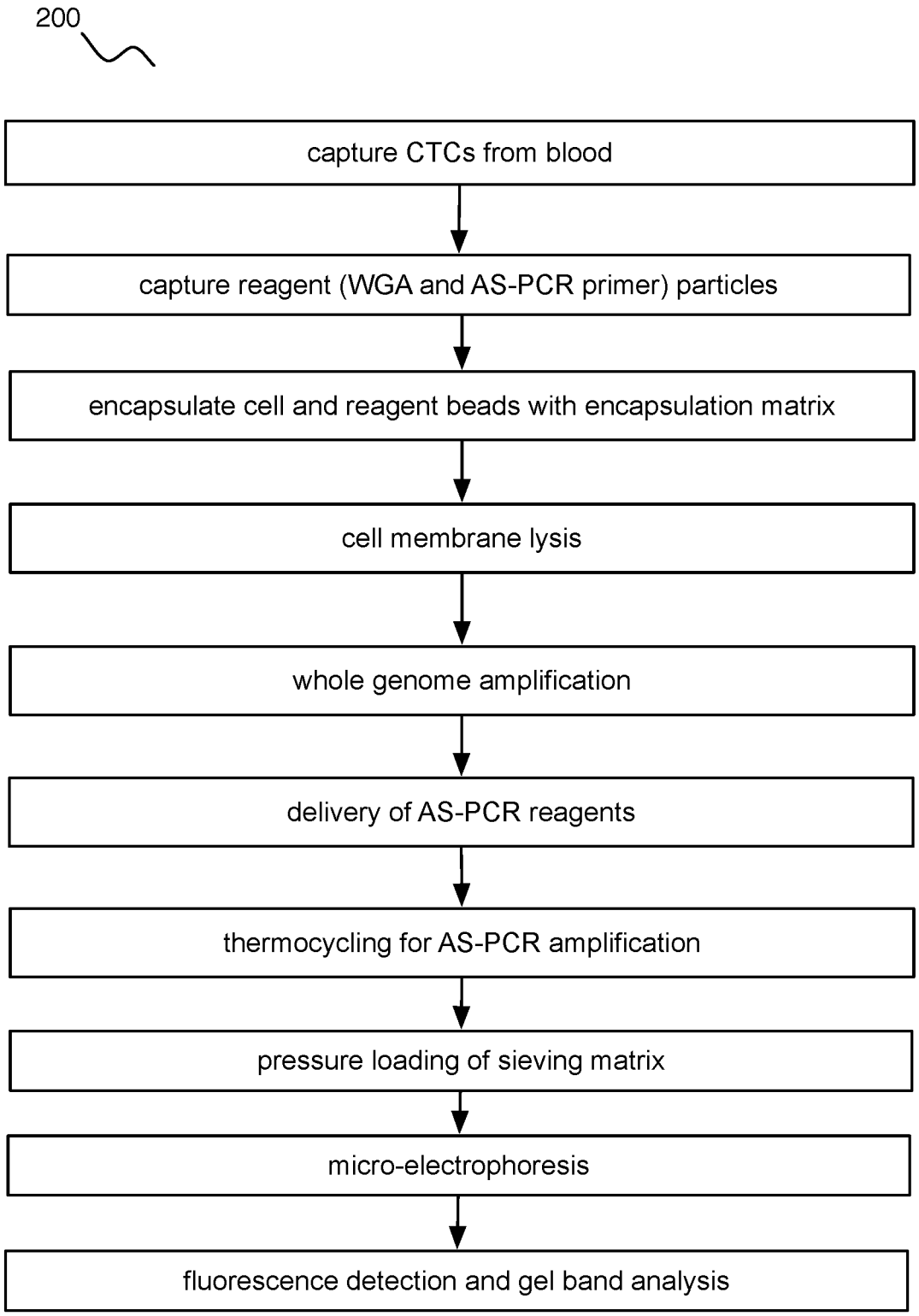
FIGS. 14A and 14B depict variations of a method for capturing and analyzing cells.
Figure 14B:
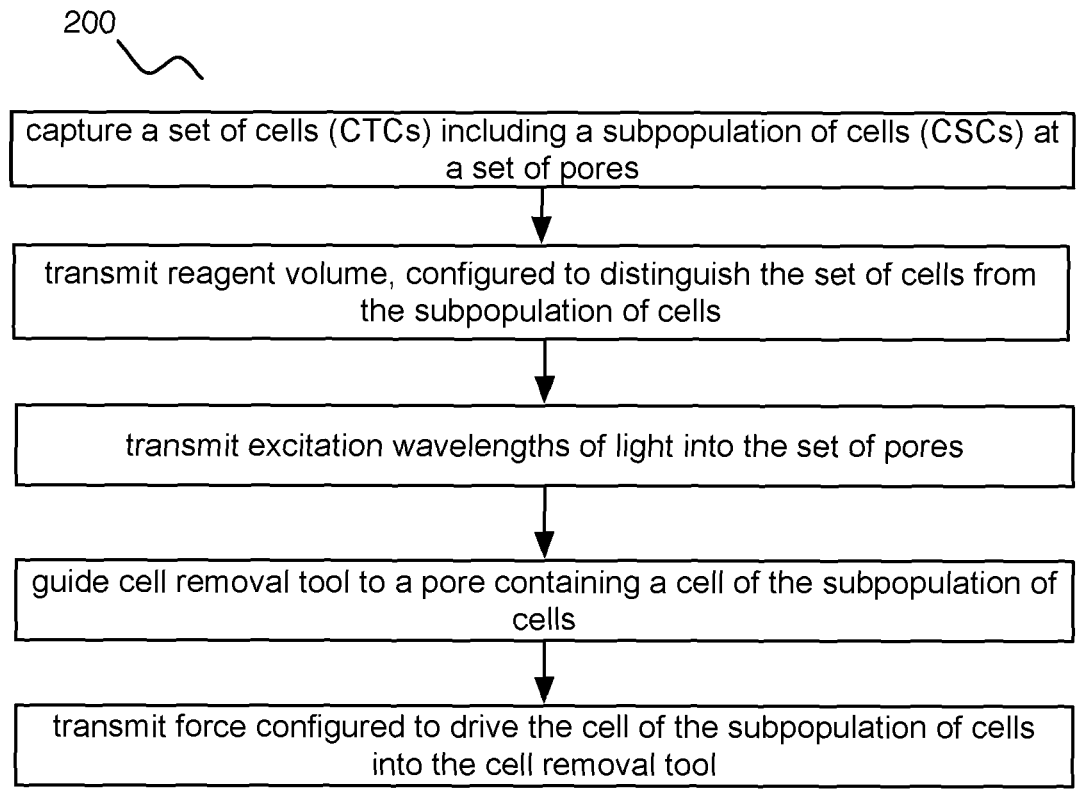

In one specific application, as shown in FIG. 14A, the method 200 can be used to isolate CTCs from a biological sample, process the CTCs on-chip for WGA and AS-PCR, and analyze the CTCs on-chip by electrophoretic separation and fluorescent detection in order to characterize the set of CTCs. In another specific application, as shown in FIG. 14B, the method 200 can be used to identify and isolate a subpopulation of CSCs from a set of CTCs, wherein the CSCs can be retrieved and analyzed by using qRT-PCR to characterize gene expression of isolated CSCs. However, in other specific applications, the method 200 can be used to process and analyze any other suitable set of cells/subpopulation of the set of cells, using any other suitable assay.

3. Integrated Platform

Figure 15:
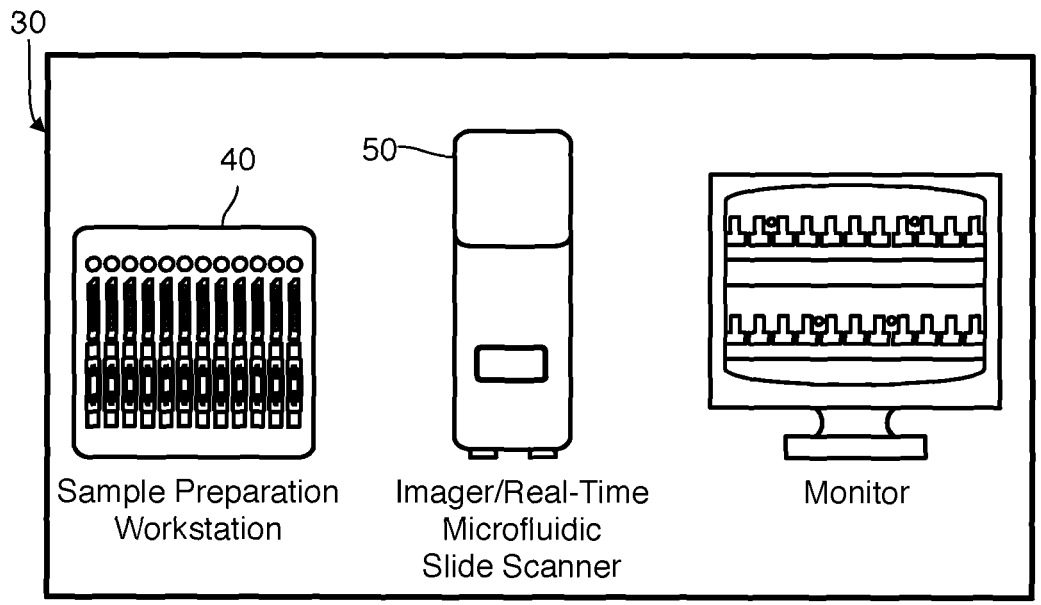
FIG. 15 is a schematic representation of an integrated platform at which embodiments of the system and/or method can be implemented.

As shown in FIG. 15, the system 100 and/or method 200 can be implemented with an integrated platform 30 including a sample workstation 40 and an imaging platform 50. The integrated platform 30 is preferably fully automated, but can alternatively be semi-automatic or manually operated. The integrated platform 30 can perform all or some the functions of pipetting, aliquoting, mixing, pumping, thermal incubation, theromocycling, monitoring, and analysis (e.g., by fluorescent detection). The integrated platform 30 can additionally automatically identify occupied chambers 113, image said chambers 113, and/or perform analyses on said chambers 113. The integrated platform 30 can additionally selectively remove cells from the system 100. In variations, the integrated platform 30 can include an embodiment of an integrated platform 50 as described in U.S. Pub. No. 2013/0190212, entitled "Cell Capture System and Method of Use" filed 25 Jul. 2012, which is incorporated herein in its entirety by this reference. However, the integrated platform 30 can be any other suitable integrated platform 30, and can additionally or alternatively perform any other suitable function. The integrated platform 30 is preferably utilized with a system 100 as described above, but can alternatively be utilized with any suitable system 100 or method 200.

The system 100 and method 200 of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The sequence listing includes the following sequences: P53 (SEQ ID NO 1), BRCA1 (SEQ ID NO 2), BRCA2 (SEQ ID NO 3), P53 Wildtype Forward Primer (SEQ ID NO 4), P53 Mutant Forward Primer (SEQ ID NO 5), P53 Common Reverse Primer (SEQ ID NO 6), BRCA1 Wildtype Forward Primer 1 (SEQ ID NO 7), BRCA1 Mutant Forward Primer 1 (SEQ ID NO 8), BRCA1 Common Reverse Primer 1 (SEQ ID NO 9), BRCA1 Wildtype Forward Primer 2 (SEQ ID NO 10), BRCA1 Mutant Forward Primer 2 (SEQ ID NO 11), BRCA1 Common Reverse Primer 2 (SEQ ID NO 12), BRCA1 Wildtype Forward Primer 3 (SEQ ID NO 13), BRCA1 Mutant Forward Primer 3 (SEQ ID NO 14), BRCA1 Common Reverse Primer 3 (SEQ ID NO 15), BRCA2 Wildtype Forward Primer (SEQ ID NO 16), BRCA2 Mutant Forward Primer (SEQ ID NO 17), and BRCA2 Common Reverse Primer (SEQ ID NO 18).

As a person skilled in the art will recognize from the previous detailed description and from the figures and claims, modifications and changes can be made to the preferred embodiments of the invention without departing from the scope of this invention defined in the following claims.

We claim:

1. A method for capturing and analyzing a population of target cells in single-cell format, comprising:
   dispensing a biological sample containing the population of target cells into an inlet channel directly fluidly coupled to a set of chambers defined within a broad surface of a substrate;
   receiving, into at least a portion of chambers of the set of chambers, exactly one of a target cell of the population of target cells from a direction substantially perpendicular to the broad surface of the substrate;
   at a fluid delivery module fluidly connected to the inlet channel, flowing a reagent fluid into the inlet channel, wherein the reagent fluid flows along the inlet channel in a direction substantially parallel to the broad surface of the substrate and accesses the set of chambers without egressing the population of target cells from the set of chambers;
   performing a biochemical process within the set of chambers, wherein the reagent fluid interacts with the population of target cells retained within the set of chambers; and extracting, from a selected chamber of the set of chambers, one of a selected target cell and intracellular content of the selected target cell, thereby enabling analysis of the population of target cells in single-cell format.

2. The method of claim 1, further comprising, prior to introducing the biological sample into the inlet channel, collecting the biological sample from an initial biological sample comprising an initial concentration of the population of target cells, wherein collecting the biological sample comprises:
  transmitting the initial biological sample through a set of pores, wherein each pore of the set of pores comprises a filter chamber;
  capturing the population of target cells within the filter chambers of the set of pores, wherein excess fluid flow of the initial biological sample through the set of pores reaches an outlet channel coupled to the downstream end of each of the pore channels only by way of the set of filter chambers;
  releasing the population of target cells captured within the filter chambers; and
  collecting the biological sample from the initial biological sample, wherein the biological sample comprises a final concentration of the population of target cells greater than the initial concentration of the population of target cells.

3. The method of claim 2, wherein the initial biological sample comprises a blood sample and the biological sample comprises an enriched volume of a subpopulation of cancer stem cells collected from the blood sample.

4. The method of claim 1, further comprising:
  upon receiving the population of target cells at the set of chambers, transmitting a population of reagent particles to the set of chambers, wherein a single reagent particle of the population of reagent particles enters a single chamber of the subset of chambers;
  at the fluid delivery module, dispensing a lysing reagent to the set of chambers, thereby lysing the population of target cells within the set of chambers to release intracellular content of the population of target cells;
  at each chamber of the set of chambers, binding a portion of the intracellular content of each target cell to each reagent particle;
  amplifying intracellular content from each captured target cell at each reagent particle; and
  removing the population of reagent particles from the set of chambers for downstream analysis.

5. The method of claim 4, wherein binding a portion of the intracellular content of each target cell to each reagent particle comprises binding intracellular content of the target cell to a surface-bound moiety of the reagent particle, wherein the surface-bound moiety comprises an oligonucleotide sequence facilitating genetic amplification of intracellular content of the target cell within the set of chambers.

6. The method of claim 4, wherein amplifying intracellular content from each target cell comprises at least one of whole genome amplification and allele-specific polymerase chain reaction.

7. The method of claim 4, wherein the chamber length of the set of chambers is configured to retain the single captured target cell and the single reagent particle, wherein the chamber length is less than 200 micron.

8. The method of claim 4, wherein the population of reagent particles define a characteristic diameter equal to 6 microns.

9. The method of claim 1, further comprising transmitting a population of reagent particles to the set of chambers, wherein a single reagent particle of the population of reagent particles is configured to interact with a portion of the set of walls of each chamber of the set of chambers.

10. The method of claim 1, wherein performing a biochemical process within the set of chambers comprises adjusting the temperature of the set of chambers according to a temperature profile, wherein the temperature profile comprises at least a first temperature for a first time duration, and a second temperature for a second time duration.

11. The method of claim 10, wherein adjusting the temperature of the set of chambers facilitates genome amplification of the target cells retained within the set of chambers.

12. The method of claim 1, further comprising encapsulating the set of chambers within an encapsulation matrix, wherein the encapsulation matrix is arranged along at least a region of the set of walls of each chamber and comprises a porous material configured to prevent egress of the population of target cells from the set of chambers.

13. The method of claim 12, wherein extracting intracellular content of the selected target cell comprises:
  at the fluid delivery module, dispensing a lysing reagent to the set of chambers, thereby lysing captured target cells within each chamber to release intracellular content of captured target cells;
  at each set of walls of each chamber of the subset of chambers, binding a portion of the intracellular content of each captured target cell to a portion of the encapsulation matrix;
  amplifying intracellular content from each captured target cell at each portion of the encapsulation matrix; and
  removing the portion of the encapsulation matrix from the selected chamber containing the selected target cell, wherein the encapsulation matrix contains amplified genetic content of the selected target cell.

14. The method of claim 1, further comprising analyzing the selected target cell of the population of target cells retained within the selected chamber of the set of chambers at an optical subsystem in communication with the substrate, comprising:
  at an automated stage of the imaging subsystem, aligning the substrate with an objective of the imaging subsystem;
  at the imaging subsystem, recording an image of a region of the substrate containing at least a subset of target cells of the population of target cells within a subset of chambers of the set of chambers;
  at a processor of the imaging subsystem, analyzing the image to obtain at least a single chamber address associated with the location of the selected chamber containing the selected target cell relative to the substrate; and
  storing, at the imaging subsystem, the chamber address, wherein the chamber address is stored in association with the selected target cell.

15. The method of claim 14, further comprising extracting the selected target cell from the selected chamber, wherein extracting the selected target cell from the selected chamber comprises:
  at the automated stage of the imaging subsystem, aligning the selected chamber with a portion of a cell removal tool according to the chamber address of the selected chamber, wherein the cell removal tool is configured to penetrate the inlet channel and facilitate extraction of the selected target cell directly from the selected chamber;

transmitting, from the cell removal tool, a negative pressure into the selected chamber; and receiving, at the cell removal tool, the selected target cell from the selected chamber into the cell removal tool.

16. The method of claim 1, wherein the set of chambers comprises 1,000,000 individual chambers.

17. The method of claim 1, wherein the chamber cross-section of each chamber in the set of chambers is arranged parallel to the broad face of the substrate, and wherein the cross-section of each chamber in the set of chambers defines a polygon.

18. The method of claim 17, wherein the cross-section of each chamber of the set of chambers defines a rectangle.

19. The method of claim 1, further comprising, prior to introducing the biological sample into the inlet channel, dispensing a priming solution into the inlet channel, wherein the priming solution substantially minimizes at least one of cell adhesion and bubble trapping through a set of fluid channels defined within the substrate.

20. The method of claim 19, wherein the priming solution comprises a solute reducing the surface tension of the priming solution below the surface tension of water.

* * * * *